United States Patent
Hartmann et al.

[11] Patent Number: 6,150,524
[45] Date of Patent: Nov. 21, 2000

[54] MORPHINE DERIVATIVES WITH ANALGESIC ACTIVITY

[75] Inventors: Michael Hartmann; Dagmar Stimmeder; Steinar Engelsen; Andreas Koch; Franz Rovenszky, all of Linz; Peter Kremminger, Asten; Michael Hutzinger, Linz, all of Austria

[73] Assignee: CeNeS Ltd., Cambridge, United Kingdom

[21] Appl. No.: 09/091,358

[22] PCT Filed: Dec. 20, 1996

[86] PCT No.: PCT/GB96/03193

§ 371 Date: Dec. 8, 1998

§ 102(e) Date: Dec. 8, 1998

[87] PCT Pub. No.: WO97/22606

PCT Pub. Date: Jun. 26, 1997

[30] Foreign Application Priority Data

| Dec. 20, 1995 | [AT] | Austria | 2069/95 |
| Dec. 20, 1995 | [AT] | Austria | 2070/95 |
| Dec. 20, 1995 | [AT] | Austria | 2071/95 |
| Dec. 20, 1995 | [AT] | Austria | 2072/95 |
| Dec. 20, 1995 | [AT] | Austria | 2073/95 |
| Dec. 20, 1995 | [AT] | Austria | 2074/95 |
| Dec. 20, 1995 | [AT] | Austria | 2075/95 |
| Dec. 20, 1995 | [AT] | Austria | 2076/95 |
| Dec. 20, 1995 | [AT] | Austria | 2077/95 |
| Dec. 20, 1995 | [AT] | Austria | 2078/95 |
| Dec. 20, 1995 | [AT] | Austria | 2079/95 |
| Dec. 20, 1995 | [AT] | Austria | 2080/95 |

[51] Int. Cl.[7] .................. A61K 31/4355; C07D 489/00; C07D 489/02

[52] U.S. Cl. ........................ 546/44; 546/46

[58] Field of Search ................ 546/46; 514/282

[56] References Cited

U.S. PATENT DOCUMENTS 3,131,185 4/1964 Lafon et al. ................ 544/125

FOREIGN PATENT DOCUMENTS

| 0 577 847 | 1/1994 | European Pat. Off. . |
| 0 632 041 | 1/1995 | European Pat. Off. . |
| 2 582 650 | 12/1986 | France . |
| 22 54 298 | 5/1974 | Germany . |
| WO 92 08459 | 5/1992 | WIPO . |
| WO 93 03051 | 2/1993 | WIPO . |
| WO 96 16063 | 5/1996 | WIPO . |

OTHER PUBLICATIONS

Progr. Drug Res., vol. 36, 1991, Basel. Boston. Berlin, pp. 49–70, XP002028172 KOLB, V.M.: "Opiate Receptors: Search for New Drugs" see the whole document.

Adv.Drug Res., vol. 16, 1987, London, pp. 281–307, XP002028173 KOLB, V.M.: "The Stereoelectronic Effects at the Opiate Receptor: Their Influence on Affinity and Intrinsic Activity" see the whole document.

*Primary Examiner*—Alan L. Rotman
*Attorney, Agent, or Firm*—Bacon & Thomas

[57] ABSTRACT

Morphine derivatives of formula (I), process for perparing them and their use and use as analgesics.

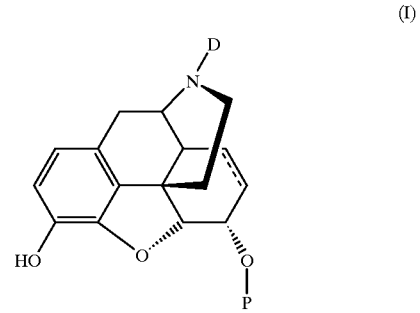

9 Claims, No Drawings

MORPHINE DERIVATIVES WITH ANALGESIC ACTIVITY

The present invention relates to new improved morphine derivatives, processes for preparing them and their use as analgesics for treating pain.

TECHNOLOGICAL BACKGROUND

Opiates are most commonly used as analgesics for treating severe chronic and acute pain. The opiate most frequently used at present for treating severe chronic or acute pain is morphine. An example of chronic pain is the pain which occurs in cancer. An example of acute pain is the pain which may occur after operations. The opiates used up until now for treating such pain are indeed highly effective but have a number of unpleasant and/or undesirable side effects, e.g. a short duration of activity, respiratory depression, nausea, constipation, diuresis and euphoria and they are also addictive.

Morphine hydrazone derivatives with analgesic activity are known from EP-A-0 242 417. EP-A-0 577 847 discloses 6-N-substituted morphine derivatives with analgesic and diuretic activity. EP-A-0 632 041 discloses 6-nicotinoylaminomorphine derivatives having analgesic activity.

A number of publications disclose preparations which attempt to avoid some of the known disadvantages of the opiates used up until now. EP-B-300 806 discloses the use of phospholipid vesicles for encapsulating opioid analgesics. EP-A-672 416, EP-A-647 448, EP-A-631 781 and WO 94/22431 disclose long-acting formulations of opiates in a hydrophobic matrix. All the formulations mentioned above have a duration of activity of from 12 to 24 hours. The disadvantages of these preparations are the delayed start of activity and the side effects, which still occur.

OBJECTIVE

There is therefore a need for compounds with powerful analgesic activity which can be taken orally, have a reduced side effects profile and wherein the analgesic activity starts quickly and is maintained throughout the desired period.

The object of the invention was therefore to provide new analgesically active compounds which, compared with known opiates, especially morphine, are more effective when administered orally and parenterally, begin their analgesic effect more rapidly, continue to act for the desired length of time and show a significant reduction in the typical side effects.

This object has been achieved by means of the new morphine derivatives of formula I.

DESCRIPTION OF THE INVENTION

The invention therefore relates to morphine derivatives (these compounds are referred to in the STN databases as morphians and this nomenclature is used in the claims) of the formula

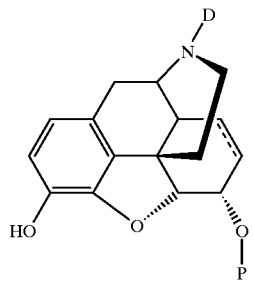

(I)

wherein
D denotes a straight-chained or branched, optionally halogenated $C_{1-4}$-alkyl group,
the dotted line may represent a chemical bond, i.e. indicates that the compounds are morphine derivatives or 7,8-dihydromorphine derivatives,
P denotes a group —C(L) ($R_1$) ($R_2$), —CO—C(L) ($R_1$) ($R_2$), —CO—N($L_1$) ($L_2$) or —$L_3$
L denotes a group —$A_1$—(C($R_3$) ($R_4$))$_k$—$A_2$—B or —$A_1$—Q—$A_2$—B
$L_1$ denotes a group —C($R_1$) ($R_2$)—B, C($R_1$) ($R_2$)—C($R_3$) ($R_4$)—B or —$R_1$,
$L_2$ denotes a group —C($R_1$) ($R_2$)—B or —C($R_1$) ($R_2$)—C($R_3$) ($R_4$)—B
$L_3$ denotes a group —Q—$A_1$—B
k is an integer from 0 to 5
$R_1$, $R_2$, $R_3$ and $R_4$ independently of one another denote hydrogen, a straight-chained or branched, saturated or unsaturated $C_{1-4}$-alkyl group or a group —$(CH_2)_x$—$OR_7$, —$(CH_2)_x$—$OC(O)R_7$, $(CH_2)_x$—F, $(CH_2)_x$—Cl, $(CHF)_x$—F, $(CHCl)_x$—Cl, $(CF_2)_x$—F, $(CCl_2)_x$—Cl
x is an integer from 0 to 2,
$A_1$ and $A_2$ independently of each other denote a group —$(CH_2)_m$—,
m is an integer from 0 to 4
Q denotes a carbo- or heterocyclic, saturated, wholly or partially unsaturated, mono- or bicyclic 5–10-membered ring system, substituted by $R^3$ and/or $R^4$, with the exception of 7, 8, 9 and 10-membered monocyclic groups,
B is a group X, CH(X) (Y) or C(X) (Y) (Z)
X, Y, Z independently of one another denote a group —$(CH_2)_n$—OH, —$(CH_2)_n$—$CO_2R_7$, —$(CH_2)_n$—CN, —$(CH_2)_n$—$CONR_5OR_6$, —$(CH_2)_n$$CONR_5R_6$, —$(CH_2)_n$—$OR_5$, —$(CH_2)_n$—$COR_5$, —$(CH_2)_n$—OC(O)$R_7$, —$(CH_2)_n$—$CONR_5OR_6$, —$(CH_2O)_n$—$NR_5C(O)R_6$, —$(CH_2)_n$—$SR_5$, —$(CH_2)_n$S(O)$R_5$, —$(CH_2)_n$—S(O)$_2NR_5R_6$, —$(CH_2)_n$—$NR_5R_6$, —$(CH_2)_n$—NHC(O)$R_5$, —$(CH_2)_n$—NHS(O)$_2R_5$, —$(CH_2)_n$—F, —$(CH_2)_n$—Cl, —$(CH_2)_n$Br, —$(CH_2)_n$—$NO_2$
n is an integer from 0 to 4,
$R_5$, $R_6$ and $R_7$ independently of one another denote hydrogen or a straight-chained or branched $C_{1-4}$-alkyl group, a $C_{1-4}$-alkenyl group or an aryl or benzyl group, and the pharmaceutically acceptable salts thereof.

DETAILED DESCRIPTION OF THE INVENTION

In formula I, D denotes a straight-chained or branched $C_{1-4}$-alkyl group which may optionally be substituted by halogen, such as Cl, F or Br. Examples of such groups include methyl, ethyl, propyl, i-propyl, butyl, i-butyl or t-butyl, trifluoromethyl, chloromethyl, bromoethyl, dibromoethyl and the like.

$A_1$ and $A_2$ independently of each other denote a group —$(CH_2)_m$— and m is an integer from 0 to 4. Examples of such groups are methylene, ethylene, propylidene and butylidene groups. $A_1$ and/or $A_2$ may also represent a bond.

Q denotes a carbo- or heterocyclic, saturated, wholly or partially unsaturated, mono- or bicyclic 5–10-membered ring system substituted by $R^3$ and/or $R^4$, with the exception of 7, 8, 9 and 10-membered monocyclic groups.

Examples of such ring systems are cyclopentyl, cyclopentenyl, cyclopentadienyl, cyclohexyl, cyclohexenyl, tetrahydrofuryl, thiolanyl, pyrrolidinyl, dihydrofuryl, dihydrothienyl, dihydropyrrolyl, dihydrooxazolyl, dihydrothiazolyl, dihydropyrazolyl, furyl, thienyl, pyrrolyl, tetrahydropyranyl, thianyl, piperidinyl, dioxanyl, morpholinyl, piperazinyl, dihydropyranyl, tetrahydropyridinyl, isoxazolyl, oxazolyl, isothiazolyl, thiazolyl, pyrazolyl, imidazolyl, triazolyl, pyranyl, cyclohexadienyl, phenyl, thiopyranyl, dihydropyridinyl, pyridyl, pyridazinyl, pyrimidinyl, pyrazinyl, oxadiazolyl, tetrazolyl, triazinyl, benzo[b]thienyl, benzofuryl, phthalimido, isobenzofuryl, indazolyl, quinolizinyl, quinolinyl or isoquinolinyl.

B denotes a group X, CH(X) (Y) or C(X) (Y) (Z), wherein X, Y, Z independently of one another denote a group —$(CH_2)_n$—OH, —$(CH_2)_n$—$CO_2R_7$, —$(CH_2)_n$—CN, —$(CH_2)_n$—$CONR_5OR_6$, —$(CH_2)_n$—$CONR_5R_6$, —$(CH_2)_n$—$COR_5$, —$(CH_2)_n$—$COR_5$, —$(CH_2)_n$—OC(O)$R_7$, —$(CH_2)_n$—$CONR_5OR_6$, —$(CH_2)_n$—$NR_5C(O)R_6$, —$(CH_2)_n$—$SR_5$, —$(CH_2)_n$—S(O)$R_5$, —$(CH_2)_n$—S(O)$_2R_5$, —$(CH_2)_n$—S(O)$_2NR_5R_6$, —$(CH_2)_n$—$NR_5R_6$, —$(CH_2)_n$—$NO_2$ and n denotes an integer from 0 to 4.

Examples of such groups are polar groups, e.g. hydroxy, halogen, carboxy, cyano, carbamoyl, alkoxy, alkyloxy, alkylthio, (alkyl)oxysulphenyl, (alkyl)oxysulphynyl, sulphamoyl, amino groups or alkyl groups substituted by these groups, such as substituted methyl, ethyl, propyl and butyl groups.

$R_1$, $R_2$, $R_3$ and $R_4$ independently of one another denote hydrogen, a straight-chained or branched, saturated or unsaturated $C_{1-4}$-alkyl group or a group —$(CH_2)_x$—$OR_7$, —$(CH_2)_x$—$OC(O)R_7$, $(CH_2)_x$—F, $(CH_2)_x$—Cl, $(CHF)_x$—F, $(CHCl)_x$—Cl, $(CF_2)_x$—F, $(CCl_2)_x$—Cl, wherein x is an integer from 0 to 2.

Examples of such groups are methyl, ethyl, propyl, isopropyl, butyl, isobutyl or tert.-butyl, ethenyl, propenyl, butenyl or hydroxyalkyl groups such as hydroxymethyl, hydroxyethyl or mono- or poly-halogenated methyl or ethyl groups, such as mono-, di- or trifluoromethyl, mono-, di-, trichloromethyl, mono-, di- or trichloroethyl, mono-, di-, tri- or pentafluoroethyl and the like.

$R_5$, $R_6$ and $R_7$ independently of one another denote hydrogen or a straight-chained or branched $C_{1-4}$-alkyl group, e.g. methyl, ethyl, propyl, isopropyl, butyl, isobutyl or tert.-butyl, an alkenyl group, such as ethenyl, propenyl, an aryl group or a benzyl group.

The compounds of general formula I according to the invention or the pharmaceutically acceptable salts thereof are powerful analgesics, both orally and parenterally. Compared with known opiates, they have a significantly better profile of side effects, namely reduced respiratory depression, less tendency to constipation, reduced nausea and less tendency to habituation (a lower addictive potential) in relation to the effective dose. These properties of the new morphine derivatives are based on their structure and their advantageous receptor and sub-receptor profile. Receptors, particularly opiate receptors, and their sub-receptors are discussed in the following publications, for example:

Handbook of Experimental Pharmacology 104/1+2, Opioids I+II, A. Herz, H. Akil, E. J. Simon Ed., Springer Verlag, Berlin 1993.

A wide therapeutic window is opened up by the pharmacological properties described above. The new compounds can therefore be used on their own or in conjunction with other active substances in the form of a conventional galenic preparation, as a therapeutic agent for the treatment and alleviation of pain.

The invention therefore also relates to pharmaceutical preparations which contain the compounds of formula I according to the invention or the salts thereof, on their own or in admixture with other therapeutically useful active substances, as well as conventional galenic excipients and/or carriers or diluents. The compounds of formula I may be administered orally in the form of tablets or capsules which contain a dosage unit of the compound together with excipients and diluents such as maize starch, calcium carbonate, dicalcium phosphate, alginic acid, lactose, magnesium stearate, primogel or talc. The tablets are produced in the conventional way by granulating the ingredients and compressing them whilst capsules are produced by packing the contents into hard gelatine capsules of a suitable size. The compounds according to the invention may also be administered in the form of suppositories which contain excipients such as beeswax derivatives, polyethyleneglycol or polyethyleneglycol derivatives, linolyic or linolenic acid esters, together with a dosage unit of the compound, and these are administered rectally.

The compounds according to the invention may also be administered by parenteral route, for example by intramuscular, intravenous or subcutaneous injection or by direct injection to the central nervous system, e.g. intrathecally. For parenteral administration they are best used in the form of a sterile aqueous solution which may contain other dissolved substances such as tonic agents, agents for adjusting the pH, preservatives and stabilisers. The compounds may be added to distilled water and the pH can be adjusted to 3 to 6 using citric acid, lactic acid or hydrochloric acid, for example. Sufficient dissolved substances such as dextrose or saline solution may be added to make the solution isotonic. Furthermore, preservatives such as p-hydroxybenzoates and stabilisers such as EDTA may be added to ensure that the solution is sufficiently durable and stable. The resulting solution can then be sterilised and transferred into sterile glass ampoules of the appropriate size to contain the desired volume of solution. The compounds according to the invention may also be administered by infusion of a parenteral formulation as described above.

The compounds according to the invention may also be administered in the form of an oily preparation, a buffered or unbuffered emulsion, a gel or a cream, by means of a transdermal plaster.

For oral administration in humans, it is assumed that the daily dose will be in the range from 0.001 to 5000 mg per day for a typical adult patient weighing 70 kg. Therefore, tablets or capsules may generally contain 0.0003 to 2000 mg of active compound, e.g. 0.01 to 500 mg, for oral administration up to three times a day. For parenteral administration, the dose may be in the range from 0.001 to 5000 mg per 70 kg per day, for example about 0.5 mg to 2500 mg.

In view of the pharmacological properties of the compounds according to the invention, the invention also relates to a method of treating pain, preferably post-operative or chronic pain, characterised in that a therapeutically effective quantity of a pharmaceutical composition as described above is administered to a patient.

PROCESS FOR PREPARATION

The invention also relates to the processes by which the compounds of formula I according to the invention may be prepared.

Ethers, i.e. compounds in which P is —C(L) (R$_1$) (R$_2$) or —L$_3$, can be prepared as follows:

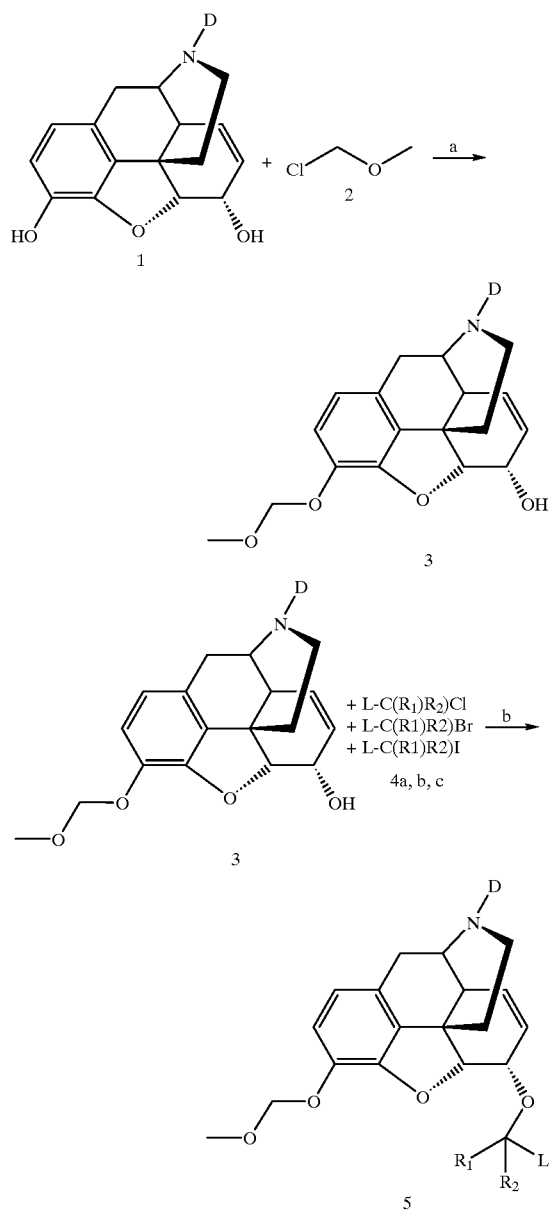

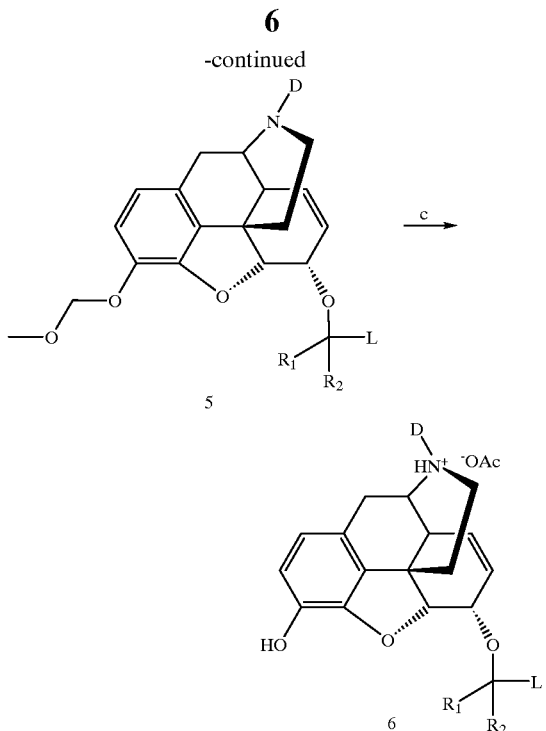

a) Na methoxide, MeOH; b) NaH, DMF; c) AcOH, H$_2$O; for compounds in which P is L$_3$ step b will use L$_3$Cl, L$_3$Br or L$_3$I.

Morphine (1) is selectively protected in the 3-position with chloromethylmethylether (2) in a suitable solvent (such as methanol) using a strong base (such as Na methoxide). Etherification is carried out according to step b with a suitable halogenated substrate (4a, 4b, 4c), after first forming the 6-alkoxide with NaH, in a suitable aprotic solvent (such as DMF). The protecting group is cleaved under conventional acidic conditions (e.g. glacial acetic acid) to obtain the desired product (6) as an acid addition salt. If desired, the free compound may be prepared by reacting with a suitable base (such as NaOH).

Esters, i.e. compounds in which P is —CO—C(L) (R$_1$) (R$_2$), can be prepared as follows:

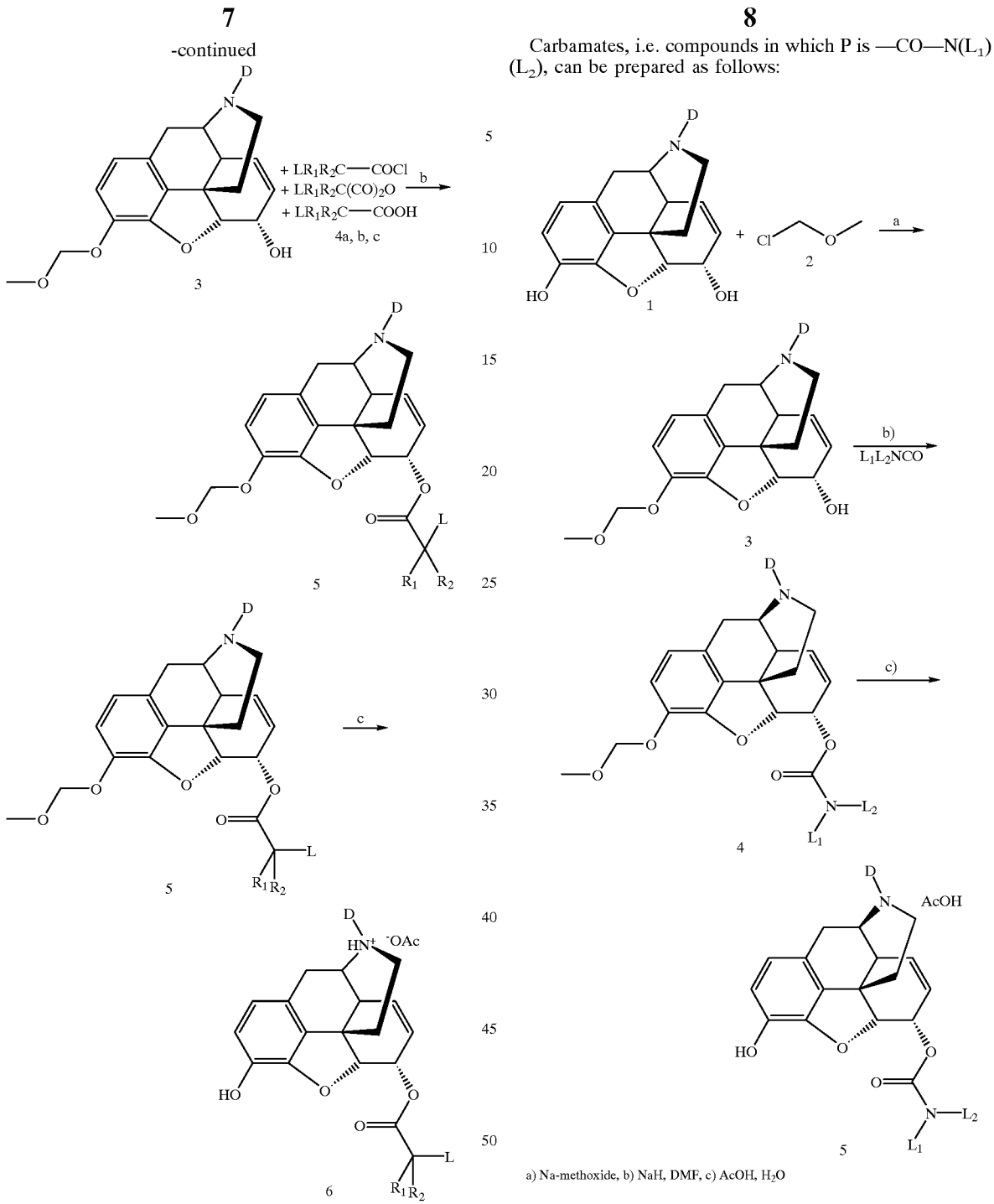

a) Na methoxide, MeOH; b) DCC, DMAP, CH$_2$Cl$_2$; c) AcOH, H$_2$O

Morphine (1) is selectively protected in the 3-position with chloromethylmethylether (2) in a suitable solvent (such as methanol) using a strong base (such as Na-methoxide). Esterification is carried out according to process step b with a suitable carboxylic acid (4a) or with a suitable carboxylic acid derivative (4b, c) using suitable activating agents such as N,N'-dichlorohexyl-carbodiimide and 4-dimethylaminopyridine in a suitable solvent (such as CH$_2$Cl$_2$). If desired, the protective group is cleaved under conventional acidic conditions (e.g. glacial acetic acid), to obtain the desired product (6) in the form of an acid addition salt. If desired, the free compound may be prepared by reacting with a suitable base (such as NaOH).

Carbamates, i.e. compounds in which P is —CO—N(L$_1$)(L$_2$), can be prepared as follows:

a) Na-methoxide, b) NaH, DMF, c) AcOH, H$_2$O

Morphine (1) is selectively protected in the 3-position with chloromethylmethylether (2) in a suitable solvent (such as methanol) using a strong base (such as Na-methoxide). The protected morphine derivative (3) thus obtained is then reacted in step b with an isocyanato derivative in the presence of a suitable reducing agent (such as NaH) and a suitable solvent (such as DMF) to obtain the protected product (4). In step c the protecting group is cleaved under conventional acidic conditions (e.g. glacial acetic acid), to obtain the desired product (5) as an acid addition salt. If desired, the free compound may be prepared by reacting with a suitable base such as NaOH.

In all cases 7,8-dihydromorphine compounds may be prepared by hydrogenation prior to the final step of cleaving the 3-position protecting group. The protected morphine compound is hydrogenated using a suitable catalyst, such as Pd on charcoal, in the presence of a solvent which is inert under the reaction conditions, such as a lower alcohol, e.g. methanol or ethanol.

The bases of formula I may be converted into their pharmaceutically acceptable salts with organic or inorganic acids in the usual way. Salt formation may be carried out, for example, by dissolving a compound of formula I in a suitable solvent such as water, acetone, acetonitrile, benzene, dimethylformamide, dimethylsulphoxide, chloroform, dioxane, methanol, ethanol, hexanol, ethyl acetate or in an aliphatic ether, such as diethylether, or mixtures of such solvents, adding an at least equivalent quantity of the desired acid, ensuring thorough mixing and, once the salt formation has ended, filtering off the precipitated salt, lyophilising it or distilling off the solvent in vacuo. If desired, the salts may be recrystallised after isolation or their solutions may be lyophilised.

Pharmaceutically acceptable salts are those with inorganic acids such as hydrochloric acid, hydrobromic acid, sulphuric acid, phosphoric acid or nitric acid, or those with organic acids such as citric acid, tartaric acid, maleic acid, fumaric acid, succinic acid, malic acid, methanesulphonic acid, aminosulphonic acid, acetic acid, benzoic acid and the like.

PHARMACOLOGICAL INVESTIGATIONS

METHOD: Haffner Test ("Tail clip test") in Mice

The Haffner test is a standard procedure for determining the pain-inhibiting effect of powerful analgesics, mostly of the opioid type, in mice. The method largely corresponds to the one described by Bianchi C. and Franceschini J. (Brit. J. Pharmacol. 9:280, 1954; Experimental observations on Haffner's method for testing analgesic drugs).

Male CD mice (from Charles River, Sulzfeld, FRG) with an average weight of 30±5 grams were used. The animals were kept under standard conditions (temperature: 22±2° C., relative humidity: 55±10%, air exchange: 15–20 times per hour and 12/12 hours light/darkness cycle). The animals had unlimited access to food and water until the test began. During the test the animals were kept singly in Makrolon Type III cages with no bedding. A 3.5 cm arterial clamp was placed about 2 cm from the base of the tail and the pain reaction time was measured in seconds. Any active attempt by the animal to remove the clamp was assessed as a pain reaction. To prevent tissue damage, the test was stopped after at most 30 seconds in every case (cut off latency). In a preliminary test, mice with a pain reaction time of less than 5 seconds (base line latency) were selected for the actual test, which was carried out at specific intervals after the administration of the drug (test latency).

Corresponding quantities of test substances were dissolved in physiological saline solution for intravenous administration or in twice distilled water for oral administration. The total volume administered was 10 ml/kg of body weight in each case. Controls were given the same solvent but with no test substance. 8–10 mice were tested in each group.

The results were plotted as individual values (seconds), mean value±scattering (seconds) per group and as the percent of the maximum possible effect (% MPE=percent of Maximum Possible Effect).

$$\% \ MPE = \frac{\text{test latency} - \text{baseline latency}}{\text{cut off latency} - \text{baseline latency}} \times 100$$

Significant differences between the control and test groups were calculated by means of an unpaired, two-sided Students T-test (*2P<0.05; **2P<0.01; 2P<0.001).

The $ED_{50}$ value describes the dosage at which 50% of the maximum possible effect (MPE) is achieved. The $ED_{50}$ value is calculated by linear regression between the dose and the % MPE.

1) ETHERS

EXAMPLE 1

6α-((4-Acetyloxy-butyl)-oxy)-4,5α-epoxy-17-methyl-morphinan-7-en-3-ol acetate

6α-((4-Acetyloxy-butyl)-oxy)-4,5α-epoxy-3-methoxymethoxy-morphinan-7-ene (133 mg, 0.3 mmol) is dissolved in water (4,5 ml) and glacial acetic acid (4,5 ml) and then stirred for 6 hours at 100° C. The volatile components are eliminated using the Rotavapor. The residue thus obtained is purified by flash chromatography (10 g silica gel; mobile phase: methylene chloride/methanol=9:1).

Yield: 100 mg 6α-((4-acetyloxy-butyl)-oxy)-4,5α-epoxy-17-methyl-morphinan-7-en-3-ol (0.22 mmol, 73%).

$^{13}$C NMR (100 MHz, CDCl$_3$) δ 176.4, 171.6, 146.3, 139.1, 131.4, 129.4, 126.9, 123.1, 119.3, 117.5, 89.2, 74.3, 68.6, 59.0, 46.3, 42.6, 41.4, 38.7, 33.8, 25.9, 25.3, 22.3, 21.4, 20.9;

The starting compound is prepared as follows:
4,5α-Epoxy-3-methoxymethoxy-17-methyl-morphinan-7-en-6α-ol Morphine (36.4 g, 120 mmol) is dissolved in absolute methanol with stirring (700 ml). A 29.7% sodium ethoxide solution in methanol (116.4 g, 640 mmol) is added dropwise to this solution. The resulting mixture is cooled to 0° C. and within 10 minutes chloromethyl-methylether (48.6 ml, 640 mmol) is added dropwise, during which time a white precipitate is formed and a temperature rise of about 5° C. is observed. The reaction mixture is poured onto water (1200 ml) and the mixture is extracted 3× with dichloromethane. The combined organic phase is dried (Na$_2$SO$_4$) and evaporated down using a Rotavapor. The product is dried for a further 4 hours at 0.01 Torr.

Yield of 4,5α-epoxy-3-methoxymethoxy-17-methyl-morphinan-7-en-6α-ol 34.25 g (86.7%).

$^{13}$C NMR (CDCl$_3$) δ 146.7, 138.3, 133.8, 132.0, 128.8, 127.9, 120.1, 118.5, 95.5, 91.3, 66.0, 58.9, 56.1, 46.4, 43.0, 42.5, 40.6, 35.5, 20.5;

6α-((4-Acetyloxy-butyl)-oxy)-4,5α-epoxy-3-methoxymethoxy-17-methyl-morphinan-7-ene NaH (50% suspension in mineral oil, 648 mg, 13.5 mmol) is washed 3× with n-pentane (8 ml) and stirred with absolute dimethylformamide at ambient temperature. Then a solution of 4,5α-epoxy-3-methoxymethoxy-17-methyl-morphinan-7-en-6α-ol (2.97 g, 9 mmol) in dimethylformamide is added. After the development of gas has ceased, a solution of 4-iodo-butylacetate (7.62 g, 31.5 ml) in dimethylformamide (12 ml) is added. The resulting mixture is stirred for a further 2 hours at ambient temperature, the reaction mixture is poured onto water (150 ml) and extracted 3× with methylene chloride. The methylene chloride phases are combined, dried over Na2SO4, filtered and concentrated by rotary evaporation. The residue thus formed is purified by flash chromatography (90 g silica gel; mobile phase: methylene chloride/methanol=9:1). Yield: 2.47 g 6α-((4-acetyloxybutyl)-oxy)-4,5α-epoxy-3-methoxymethoxy-17-methyl-morphinan-7-ene (5.58 mmol, 62%).

$^{13}$C NMR (CDCl$_3$) δ 171.0, 148.6, 138.8, 131.2, 130.8, 128.7, 128.5, 118.9, 118.3, 96.0, 89.7, 74.4, 68.3, 64.2, 58.8, 56.1, 46.4, 43.2, 43.0, 41.1, 35.8, 26.3, 25.4, 20.8, 20.5;

EXAMPLE 2

4,5α-Epoxy-6α((4-hydroxy-butyl)-oxy)-17-methyl-morphinan-7-en-3-ol acetate

Aqueous 1 M NaOH (0.87 ml, 0.87 mmol) is added to a solution of 6α-((4-acetyloxy-butyl)-4,5α-epoxy-17-methyl-morphinan-7-en-3-ol (100 mg, 0.218 mmol) in water (2 ml). After 15 minutes at ambient temperature the solution is concentrated in a Rotavapor. The residue thus formed is dissolved in a mixture of water (0.3 ml) and glacial acetic acid and lyophilised.

Yield: 75 mg (0.21 mmol, 82%) 4,5α-epoxy-6α-((4-hydroxy-butyl)-oxy)-17-methyl-morphinan-7-en-3-ol acetate $^{13}$C NMR (CDCl$_3$) δ 175.6, 146.1, 139.2, 130.0, 129.5, 128.4, 124.7, 120.1, 119.0, 89.0, 74.0, 69.6, 63.1, 59.0, 46.3, 42.5, 42.2, 39.6, 34.4, 31.0, 28.9, 21.8, 20.9.

The following were prepared analogously to Example 1 or 2

EXAMPLE 3

6α-((4-benzoyloxy-butyl)oxy)-4,5α-epoxy-3-methoxymethoxy-17-methyl-morphinan-7-ene ES MS m/z 506 (M+H$^+$)

EXAMPLE 4

6α-((4-benzoyloxy-butyl)-oxy)-4,5α-epoxy-17-methyl-morphinan-7-en-3-ol acetate $^{13}$C NMR (100 MHz, CDCl$_3$) δ 176.2, 167.5, 146.5, 139.4, 133.3, 132.3, 130.6, 129.9, 129.4, 128.7, 126.4, 119.9, 118.0, 89.5, 69.0, 65.4, 60.2, 47.1, 42.8, 42.1, 38.9, 33.7, 26.4, 25.8, 22.3, 22.0, 20.1.

EXAMPLE 5

4,5α-Epoxy-3-methoxymethoxy-17-methyl-6α-((4-pivaloyloxy-butyl)-oxy)-morphinan-7-ene $^{13}$C NMR (100 MHz, CDCl$_3$) δ 178.4, 148.7, 139.4, 132.1, 130.2, 126.4, 126.2, 119.2, 119.0, 96.0, 89.1, 73.9, 68.7, 64.1, 59.9, 56.2, 46.9, 42.4, 39.3, 38.6, 36.3, 34.1, 27.1, 26.4, 25.4, 21.5.

EXAMPLE 6

4,5α-Epoxy-17-methyl-6α-((4-pivaloyloxy-butyl)-oxy)-morphinan-7-en-3-ol acetate $^{13}$C NMR (100 MHz, CDCl$_3$) δ 179.2, 176.1, 146.3, 138.8, 131.2, 129.7, 127.4, 124.0, 119.4, 117.3, 89.6, 74.6, 68.6, 64.3, 59.0, 46.3, 43.0, 41.8, 39.4, 38.8, 34.4, 27.2, 25.9, 25.5, 22.1, 21.2.

EXAMPLE 7

6α-((5-Acetyloxy-pentyl)-oxy)-4,5α-epoxy-3-methoxymethoxy-17-methyl-morphinan-7-ene $^{13}$C NMR (100 MHz, CDCl$_3$) δ 171.2, 148.8, 139.5, 132.2, 130.6, 126.9, 126.8, 119.4, 119.1, 96.2, 89.4, 74.2, 69.2, 64.6, 59.9, 56.4, 47.0, 42.7, 42.6, 39.6, 34.5, 29.8, 29.3, 28.5, 22.7, 21.6, 21.1.

EXAMPLE 8

6α-((5-Acetyloxy-pentyl)-oxy)-4,5α-epoxy-17-methyl-morphinan-7-en-3-ol acetate $^{13}$C NMR (100 MHz, CDCl$_3$) δ 175.8, 171.3, 146.3, 139.3, 131.9, 128.7, 125.8, 121.8, 119.6, 118.1, 88.9, 74.0, 69.5, 64.3, 60.0, 50.2, 46.8, 42.2, 41.3, 38.0, 32.8, 29.1, 28.2, 22.4, 21.8, 20.8.

EXAMPLE 9

4,5α-Epoxy-3-methoxymethoxy-6α-((5-hydroxypentyl)-oxy)-17-methyl-morphinan-7-ene $^{13}$C NMR (100 MHz, CDCl$_3$) δ 147.9, 138.3, 130.9, 130.0, 126.6, 126.58, 118.6, 118.2, 95.4, 88.8, 73.5, 68.6, 61.6, 58.8, 55.6, 49.4, 46.0, 42.1, 41.9, 39.0, 33.8, 31.7, 28.8, 21.7.

EXAMPLE 10

4,5α-Epoxy-6α-(5-hydroxypentyl)-oxy)-17-methyl-morphinan-7-en-3-ol acetate $^{13}$C NMR (100 MHz, D$_2$O) δ 184.0, 148.5, 140.9, 132.1, 129.0, 126.3, 122.9, 120.4, 91.4, 76.2, 72.5, 64.3, 62.9, 49.6, 43.4, 40.3, 34.7, 33.7, 31.2, 26.0, 24.3;

EXAMPLE 11

4,5α-Epoxy-6α-((3-ethoxycarbonyl-(E)-prop-2-enyl)-3-methoxymethoxy-17-methyl-morphinan-7-ene $^{13}$C NMR (100 MHz, d$_6$-DMSO) δ 164.6, 148.3, 138.8, 135.2, 134.0, 130.6, 130.1, 125.4, 125.0, 119.4, 119.1, 95.4, 91.4, 66.2, 65.7, 60.7, 59.7, 55.9, 55.4, 50.8, 41.2, 32.8, 29.1, 23.5, 14.2.

EXAMPLE 12

4,5α-Epoxy-6α-(3-ethyloxycarbonyl-(E)-prop-2-enyl)-17-methyl-morphinan-7-en-3-ol acetate $^3$C NMR (100 MHz, D$_2$O) δ 168.2, 146.9, 139.8, 135.1, 133.9, 133.4, 130.7, 126.8, 124.3, 121.9, 119.5, 91.7, 68.7, 67.1, 64.0, 62.0, 57.6, 52.7, 43.0, 42.9, 34.6, 30.8, 25.0, 24.8, 15.0.

EXAMPLE 13

6α-((N,N-Diethylcarbamoyl-methyl)-oxy)-4,5α-epoxy-3-methoxymethoxy-17-methyl-morphinan-7-ene $^{13}$C NMR (100 MHz, CDCl$_3$) δ 167.4, 147.6, 138.0, 130.3, 129.4, 127.9, 127.8, 118.1, 117.2, 95.1, 88.5, 73.5, 67.6, 58.0, 55.3, 45.5, 42.4, 42.1, 40.5, 40.0, 39.0, 34.8, 19.7, 13.3, 11.8.

EXAMPLE 14

6α-((N,N-Diethylcarbamoyl-methyl)-oxy)-4,5α-epoxy-17-methyl-morphinan-7-en-3-ol acetate $^{13}$C NMR (100 MHz, CDCl$_3$) δ 176.6, 169.1, 146.5, 139.7, 130.6, 129.9, 128.3, 123.9, 119.9, 118.2, 89.6, 74.0, 68.4, 59.4, 46.7, 42.7, 42.0, 41.8, 40.6, 39.2, 34.2, 22.6, 21.5, 14.5, 13.0.

EXAMPLE 15

6α-((N,N-Dimethylcarbamoyl-methyl)-oxy)-4,5α-epoxy-3-methoxymethoxy-17-methyl-morphinan-7-ene $^{13}$C NMR (100 MHz, CDCl$_3$) δ 169.1, 148.4, 138.9, 131.1, 130.2, 128.8, 128.7, 119.0, 118.0, 95.9, 89.3, 74.4, 68.5, 58.8, 56.1, 46.4, 43.2, 42.9, 40.8, 36.6, 35.6, 35.5, 20.6.

EXAMPLE 16

6α-((N,N-Diethylcarbamoyl-methyl)-oxy)-4,5α-epoxy-17-methyl-morphinan-7-en-3-ol acetate $^{13}$C NMR (100 MHz, CDCl$_3$) δ 176.1, 169.6, 146.1, 139.5, 130.6, 129.3, 127.5, 122.9, 119.8, 118.3, 89.3, 73.5, 68.0, 59.2, 46.4, 42.1, 41.3, 38.3, 36.7, 35.7, 33.3, 21.9, 21.4.

EXAMPLE 17

6α-(((4S)-2,2-Dimethyl-1,3-dioxolan-4-yl)-methyloxy)-4,5α-epoxy-3-methoxymethoxy-17-methyl-morphinan-7-ene $^3$C NMR (100 MHz, CDCl$_3$) δ 148.6, 138.9, 130.6, 128.73, 128.71, 119.1, 118.4, 109.2, 96.1, 89.7, 74.9, 69.4, 66.8, 58.9, 56.3, 46.5, 43.3, 43.1, 41.1, 35.9, 26.7, 25.5, 20.5.

EXAMPLE 18

6α-((2R)-2,3-Dihydroxy-propyloxy)-4,5α-epoxy-17-methyl-morphinan-7-en-3-ol acetate $^{13}$C NMR (100 MHz, D$_2$O) δ 181.8, 148.3, 140.7, 133.7, 131.8, 128.6, 126.0, 123.0, 120.5, 91.0, 76.6, 73.2, 73.1, 65.3, 63.3, 49.9, 44.3, 43.6, 41.2, 35.2, 24.6, 23.6.

EXAMPLE 19

6α-(((4R)-2,2-Dimethyl-1,3-dioxolan-4-yl)-methyloxy)-4,5α-epoxy-3-methoxymethoxy-17-methyl-morphinan-7-ene $^{13}$C NMR (100 MHz, CDCl$_3$) δ 148.6, 138.9, 131.3, 130.6, 128.73, 128.71, 119.1, 118.4, 109.2, 96.1, 89.7, 74.9, 69.4, 66.8, 58.9, 56.3, 46.5, 43.3, 43.1, 41.1, 35.9, 26.7, 25.5, 20.5.

EXAMPLE 20

6α-((2S)-2,3-Dihydroxy-propyloxy)-4,5α-epoxy-17-methyl-morphinan-7-en-3-ol acetate $^{13}$C NMR (100 MHz, D$_2$O) δ 181.2, 148.3, 140.7, 133.7, 131.8, 128.6, 125.9, 123.0, 120.5, 91.0, 76.7, 73.3, 65.3, 63.3, 49.9, 44.3, 43.6, 41.2, 35.3, 24.3, 23.6.

EXAMPLE 21

4,5-Epoxy-6α-(5-ethyloxycarbonyl-pentyloxy)-3-methoxymethoxy-17-methyl-morphinan-7-ene $^{13}$C NMR (100 MHz, CDCl$_3$) δ 173.6, 162.4, 148.7, 139.1, 131.6, 130.8, 127.5, 127.4, 119.0, 118.7, 96.0, 89.5, 74.2, 69.0, 60.1, 59.4, 56.2, 46.7, 42.9 42.7, 40.2, 35.0, 34.2, 29.5, 25.7, 24.7, 21.0, 14.2.

EXAMPLE 22

4,5α-Epoxy-6α-(5-ethyloxycarbonyl-pentyloxy)-17-methyl-morphinan-7-en-3-ol acetate $^{13}$C NMR (100 MHz, CDCl$_3$) δ 174.5, 146.7, 139.1, 132.1, 129.8, 127.1, 123.8, 119.8, 117.8, 89.9, 74.8, 69.6, 60.7, 60.0, 47.1, 43.2, 42.4, 39.6, 34.6, 34.4, 29.6, 26.0, 24.8, 21.8, 14.5.

EXAMPLE 23

6α-((5-Carboxyl-pentyl)-oxy)-4,5α-epoxy-17-methyl-morphinan-7-en-3-ol acetate $^{13}$C NMR (100 MHz, d$_6$-dmso) δ 174.9, 146.4, 138.5, 130.9, 130.7, 129.3, 125.4, 118.4, 116.3, 88.9, 74.4, 68.3, 58.1, 46.1, 43.2, 42.8, 35.6, 34.0, 29.3, 25.4, 24.6, 20.2.

EXAMPLE 24

4,5α-Epoxy-6α-((4-ethyloxycarbonyl-butyl)-oxy)-3-methoxymethoxy-17-methyl-morphinan-7-ene $^{13}$C NMR (100 MHz, CDCl$_3$) δ 173.9, 149.0, 139.3, 131.6, 131.2, 128.2, 128.1, 119.3, 118.9, 96.3, 89.8, 74.6, 68.9, 60.3, 59.5, 56.5, 46.9, 43.3, 43.1, 40.8, 35.6, 34.2, 29.5, 21.9, 21.2, 14.4.

EXAMPLE 25

4,5α-Epoxy-6α-((4-ethyloxycarbonyl-butyl)-oxy)-17-methyl-morphinan-7-en-3-ol acetate $^{13}$C NMR (100 MHz, CDCl$_3$) δ 176.1, 174.3, 146.2, 139.1, 132.0, 129.2, 126.2, 122.7, 119.5, 117.7, 89.0, 74.0, 68.5, 60.5, 59.6, 46.6, 42.5, 41.5, 38.5, 33.8, 33.5, 29.0, 22.0, 21.8, 21.6, 13.6.

EXAMPLE 26

4,5α-Epoxy-6α-(4-cyanobutyloxy)-3-methoxymethoxy-17-methyl-morphinan-7-ene $^{13}$C NMR (100 MHz, CDCl$_3$) δ 148.7, 139.3, 131.3, 131.2, 128.52, 128.49, 120.2, 129.3, 118.4, 96.2, 89.6, 74.5, 67.9, 59.3, 56.5, 46.8, 43.3, 43.1, 40.9, 35.8, 28.9, 22.9, 21.0, 17.0.

EXAMPLE 27

4,5α-Epoxy-6α-(4-cyanobutyloxy)-17-methyl-morphinan-7-en-3-ol acetate $^{13}$C NMR (100 MHz, CDCl$_3$) δ 176.6, 146.6, 139.2, 131.6, 129.9, 127.4, 123.9, 120.3, 119.8, 117.7, 89.6, 74.6, 68.4, 59.5, 46.8, 43.0, 42.0, 39.2, 34.2, 28.9, 22.8, 22.5, 21.7, 17.2.

EXAMPLE 28

4,5α-Epoxy-6α-((4-methoxycarbonyl-butyl)-oxy)-3-methoxymethoxy-17-methyl-morphinan-7-en $^{13}$C NMR (100 MHz, CDCl$_3$) δ 173.9, 148.7, 138.9, 131.2, 1131.1, 128.3, 128.1, 118.9, 118.5, 96.1, 89.6, 74.4, 68.5, 59.0, 56.2, 51.3, 46.5, 43.1, 42.9, 40.8, 35.6, 33.7, 29.3, 21.7, 20.7.

EXAMPLE 29

4,5α-Epoxy-6α-((4-methoxycarbonyl-butyl)-oxy)-17-methyl-morphinan-7-en-3-ol acetate $^{13}$C NMR (100 MHz, CDCl$_3$) δ 176.4, 175.0, 146.6, 139.0, 131.7, 130.0, 127.6, 124.4, 119.7, 117.6, 89.7, 74.6, 68.7, 59.5, 52.0, 46.8, 43.3, 42.3, 39.8, 34.7, 33.9, 29.3, 22.5, 22.1, 21.5.

EXAMPLE 30

6α-((4-Carboxyl-butyl)-oxy)-4,5α-epoxy-17-methyl-morphinan-7-en-3-ol acetate $^{13}$C NMR (100 MHz, d$_6$-dmso) δ 175.0, 146.4, 138.6, 130.7, 129.3, 125.3, 118.5, 116.3, 88.9, 74.34, 68.1, 58.0, 48.7, 46.0, 43.1, 40.7, 35.6, 34.1, 29.0, 21.6, 20.1.

EXAMPLE 31

6α-((2-Acetyloxy-pentyl)-oxy)-4,5α-epoxy-3-methoxymethoxy-17-methyl-morphinan-7-ene $^{13}$C NMR (100 MHz, CDCl$_3$) δ 170.5, 148.6, 139.7, 132.8, 129.5, 124.9, 124.5, 119.4, 95.9, 95.8, 88.7,88.6, 73.5, 70.6, 69, 60.5, 56.2, 47.2, 42.0, 41.8, 38.0, 32.4, 25.7, 24.2, 22.1, 21.2, 19.8, 13.6.

EXAMPLE 32

6α-((2-Acetyloxy-pentyl)-oxy)-4,5α-epoxy-17-methyl-morphinan-7-en-3-ol acetate $^{13}$C NMR (100 MHz, CDCl$_3$) δ 175.7, 172.1, 146.5, 139.8, 133.0, 128.9, 125.3, 121.6, 120.1, 118.4, 89.2, 74.2, 71.3, 71.0, 69.3, 68.9, 61.0, 59.6, 47.6, 42.4, 42.0, 38.2, 32.9, 32.7, 25.8, 25.4, 24.6, 22.5, 21.8, 21.7, 21.6, 20.3, 20.1, 14.0.

EXAMPLE 33

6α-((2-Hydroxypentyl)-oxy)-4,5α-epoxy-17-methyl-morphinan-7-en-3-ol acetate $^{13}$C NMR (100 MHz, D$_2$O) δ 148.4, 140.7, 133.9, 13.9, 128.6, 126.0, 123.0, 120.5, 91.2, 76.0, 72.5, 70.3, 63.3, 50.0, 44.3, 43.7, 41.3, 37.1, 35.3, 27.8, 24.5, 23.6.

EXAMPLE 34

6α-((5-Acetyloxy-4-methyl-pentyl)-oxy)-4,5α-epoxy-3-methoxy-methoxy-17-methyl-morphinan-7-ene $^{13}$C NMR (100 MHz, CDCl$_3$) δ 171.0, 162.4, 148.6, 139.6, 132.6, 129.8, 125.4, 125.1, 119.3, 119.2, 95.9, 88.9, 73.7, 69.5, 69.4, 69.2, 60.3, 56.2, 47.1, 42.1, 42.1, 38.5, 36.3, 33.3, 32.3, 31.3, 29.7, 29.7, 27.1, 21.9, 20.8, 16.7.

EXAMPLE 35

6α-((5-Acetyloxy-4-methyl-pentyl)-oxy)-4,5α-epoxy-17-methyl-morphinan-7-en-3-ol acetate $^{13}$C NMR (100 MHz, CDCl$_3$) δ 175.3, 171.6, 171.5, 146.3, 139.1, 132.4, 132.3, 128.8, 125.5, 125.4, 122.0, 121.9, 119.8, 118.0, 117.0, 89.3, 89.2, 74.0, 70.0, 69.7, 69.4, 69.3, 60.4, 47.1, 42.3, 41.7, 38.2, 32.9, 32.4, 32.2, 29.9, 29.6, 27.1, 26.9, 22.0, 21.4, 20.9, 16.8.

EXAMPLE 36

4,5α-Epoxy-6α-((5-hydroxy-4-methyl-pentyl)-oxy)-17-methyl-morphinan-7-en-3-ol acetate $^{13}$C NMR (100 MHz, d$_6$-dmso) δ 172.2, 146.4, 139.1, 131.9, 129.5, 126.8, 122.9, 119.0, 117.1, 88.2, 73.9, 69.0, 66.3, 59.3, 46.2, 42.2, 41.0, 40.2, 40.0, 35.3, 29.5, 27.1, 21.1, 16.9.

EXAMPLE 37

6α-((3-Acetyloxy-propyl)-oxy)-4,5α-epoxy-3-methoxymethoxy-17-methyl-morphinan-7-ene $^{13}$C NMR (100 MHz, d$_6$-dmso) δ 170.7, 148.4, 138.7, 130.7, 128.3, 128.2, 118.8, 118.2, 95.8, 89.3, 74.2, 68.0, 65.3, 61.5, 58.8, 56.0, 46.4, 42.7, 40.6, 35.4, 29.0, 20.7, 20.5.

EXAMPLE 38

6α-((3-Acetyloxy-propyl)-oxy)-4,5α-epoxy-17-methyl-morphinan-7-en-3-ol acetate $^{13}$C NMR (100 MHz, CDCl$_3$) δ 176.0, 172.3, 146.1, 138.6, 131.0, 129.9, 128.0, 124.7, 124.7, 119.4, 117.3, 89.0, 74.3, 73.8, 64.8, 61.7, 59.0, 46.4, 43.1, 42.3, 40.1, 35.0, 29.2, 21.0, 20.9.

EXAMPLE 39

4,5α-Epoxy-6α-((3-hydroxypropyl)-oxy)-17-methyl-morphinan-7-en-3-ol acetate $^{13}$C NMR (100 MHz, d$_6$-dmso) δ 176.2, 145.6, 139.0, 131.0, 129.6, 127.3, 124.1, 119.9, 118.6, 88.3, 72.7, 67.7, 62.0, 59.1, 46.5, 42.0, 41.8, 38.9, 34.2, 31.3, 22.2, 20.9.

EXAMPLE 40

6α-((6-Acetyloxy-hexyl)-oxy)-4,5α-epoxy-3-methoxymethoxy-17-methyl-morphinan-7-ene $^{13}$C NMR (100 MHz, d$_6$-dmso) δ 170.7, 148.4, 138.7, 130.7, 128.3, 128.2, 118.8, 118.2, 95.8, 89.3, 74.2, 68.0, 65.3, 61.5, 58.8, 56.0, 46.4, 42.7, 40.6, 35.4, 29.0, 20.7, 20.5.

EXAMPLE 41

6α-((6-Acetyloxy-hexyl)-oxy)-4,5α-epoxy-17-methyl-morphinan-7-en-3-ol acetate $^{13}$C NMR (100 MHz, CDCl$_3$) α 171.3, 146.4, 138.7, 138.6, 131.0, 129.8, 127.7, 124.3, 119.4, 117.4, 114.6, 89.8, 74.7, 69.7, 64.4, 59.2, 46.5, 43.1, 42.2, 39.8, 34.6, 29.6, 28.5, 25.7, 21.1. 20.9.

EXAMPLE 42

4,5α-Epoxy-17-methyl-6α-((6-hydroxy-hexyl)-oxy)-morphinan-7-en-3-ol acetate $^{13}$C NMR (100 MHz, CDCl$_3$) δ 146.3, 138.9, 130.7, 129.8, 128.0, 124.2, 119.6, 117.9, 89.8, 75.0, 69.9, 62.4, 59.0, 46.3, 43.1, 42.1, 39.7, 34.5, 31.7, 29.1, 24.7, 21.2.

EXAMPLE 43

6α[2'(2-Dimethyl-1,3-dioxolan-4-yl)ethyl)oxy-4,5α-epoxy-3-methoxymethoxy-17-methyl-morphin-7-ene

C$_{26}$H$_{35}$NO$_6$

MW: 457.57 gmol$^{-1}$

Diastereomeric mixture at 3'-C; $^{13}$C-data for both isomers.

$^{13}$CNMR(100 MHz, CDCL$_3$) δ 162.5, 148.6, 148.5 138.9, 138.8, 131.2, 130.8, 130.7, 128.7, 128.6, 128.5, 118.9, 118.2, 118.1, 108.2, 96.0, 95.9, 89.6, 89.5, 74.6, 74.5, 74.2, 73.8, 69.8, 69.96, 65.8, 65.7, 58.8, 56.2, 50.5, 46.4, 43.2, 43.0, 41.0, 35.8, 34.0, 26.9, 26.8, 25.7, 20.6.

EXAMPLE 44

6α-[3',4'-Dihydroxybutyl]oxy-4,5α-epoxy-17-methyl-morphin-7-en-3-ol acetate

C$_{33}$H$_{31}$NO$_7$

MW: 433.51 gmol$^{-1}$

Diastereomeric mixture at 3'-C; $^{13}$C-data for both isomers.

$^{13}$C NMR (100 MHz CDCl$_3$) δ 176.4, 145.9, 145.7, 139.2, 139.1, 131.2, 130.8, 129.4, 129.3, 127.1, 126.6, 123.4, 123.0, 120.1, 119.9, 118.9, 118.3,88.5, 88.1, 73.3, 72.9, 71.7, 70.0, 66.7, 66.5, 66.3, 65.4, 59.2, 59.1, 46.5, 46.4, 41.9, 41.8, 41.4, 41.3, 38.3, 38.2, 33.5, 33.4, 33.1, 33.0, 22.0, 21.3.

EXAMPLE 45

6α-[2'(2-Dimethyl-1,3-dioxolan-4(R)-yl)ethyl]oxy-4,5α-epoxy-17-methyl-morphin-7-ene $C_{26}H_{55}NO_6$
MW: 457.51 gmol$^{-1}$
$^{13}$CNMR(100MHz, CDCl$_3$) δ 148.6, 138.9, 131.2, 130.9, 128.6, 128.5, 119.0, 118.3, 108.4, 96.0, 89.6, 74.6, 73.8, 69.7, 65.7, 59.0, 56.2, 46.5, 43.2, 43.0, 41.0, 35.8, 34.1, 26.9, 25.7, 20.6.

EXAMPLE 46

6α-[(3'R)-3',4'-Dihydroxybutyl]oxy-4,5α-epoxy-17-methyl-morphin-7-en-3-ol acetate $C_{23}H_{31}NO_7$
MW: 433.51 gmol$^{-1}$
$^{13}$CNMR (100 MHz, CDCl$_3$) δ 176.5, 145.8, 138.9, 130.5, 129.7, 127.8, 124.2, 120.0, 118.6, 88.3, 73.5, 71.6, 66.6, 6.3, 59.0, 46.4, 42.2, 41.9, 39.1, 34.2, 33.2, 22.3, 21.0.

EXAMPLE 47

6α-[2'(2-Dimethyl-1,3-dioxolan-4(S)-yl)ethyl]oxy-4,5α-epoxy-17-methyl-morphin-7-ene $C_{26}H_{35}NO_6$
MW: 457.51 gmol$^{-1}$
$^{13}$CNMR(100 MHz, CDCl$_3$) δ 148.5, 138.9, 131.2, 130.8, 128.6, 128.5, 118.9, 118.1, 108.2, 96.0, 89.5, 74.5, 74.2, 69.7, 65.7, 58.8, 56.1, 46.4, 43.2, 43.0, 41.0, 35.8, 34.0, 26.8, 25.7, 20.6.

EXAMPLE 48

6α-[(3'S)-3',4'-Dihydroxybutyl]oxy-4,5α-epoxy-17-methyl-morphin-7-en-3-ol acetate $C_{23}H_{31}No_7$
MW: 433.51 gmol$^{-1}$
$^{13}$CNMR(100 MHz, CDCl$_3$) δ 176.6, 145.7, 139.0, 130.9, 129.6, 127.1, 123.7, 119.8, 118.0, 88.7, 73.0, 70.0, 66.5, 65.3, 59.1, 46.4, 42.1, 41.8, 38.7, 33.9, 33.1, 22.3, 21.1.

EXAMPLE 49

4,5α-Epoxy-6α-[(methoxycarbonyl)propyl]oxy-3-methoxymethoxy-17-methyl-morphin-7-ene $C_{24}H_{31}NO6$
$^{13}$CNMR(100 MHz, CDCl$_3$) δ 174.2, 148.0, 138.9, 131.1, 129.5, 128.8, 128.6, 119.3, 118.6, 96.1, 88.5, 68.3, 59.1, 56.3, 46.6, 43.0, 42.9, 40.7, 35.4, 20.6, 12.9, 8.6, 8.5.

EXAMPLE 50

4,5α-Epoxy-6α-[(methoxycarbonyl)propyl]oxy-17-methyl-morphin-7-en-3-ol acetate $C_{24}H_{31}NO_7$
MW: 445.49 gmol$^{-1}$
$^{13}$CNMR(100 MHz, CDCl$_3$) δ 176.2, 174.2, 145.5, 138.6, 129.6, 129.0, 128.3, 124.5, 119.7, 117.1, 88.2, 67.9, 59.0, 46.5, 42.5, 41.9, 39.1, 34.1, 22.1, 21.0, 12.8, 8.7.

EXAMPLE 51

6α-[3'-Acetoxy-propyl]oxy-4,5α-epoxy-3-methoxymethoxy-17-methyl-morphin-7-ene $C_{24}H_{31}NO_6$
MW: 429.52 gmol$^{-1}$
$^{13}$CNMR(100 MHz, CDCl$_3$) δ 170.8, 148.5, 138.7, 131.0, 130.6, 128.5, 128.4, 118.8, 118.2, 95.8, 89.4, 74.3, 65.4, 61.5, 58.7, 46.2, 43.1, 42.8, 40.8, 35.6, 29.0, 20.7, 20.4.

EXAMPLE 52

6α-[3'-Acetoxy-propyl]oxy-4,5α-epoxy-17-methyl-morphin-7-en-3-ol acetate $C_2H_{31}NO_7$
MW: 445.52 gmol$^{-1}$
$^{13}$CNMR(100 MHz, CDCl$_3$) δ 176.2, 172.4, 146.1, 139.0, 131.6, 129.4, 126.9, 123.3, 119.5, 117.5, 88.6, 73.9, 64.7, 61.7, 59.1, 46.3, 42.6, 41.5, 38.8, 34.0, 29.1, 22.1, 21.3, 21.0.

Example A:

TABLE 1

Haffner test in mice, % MPE, ED$_{50}$ values, i.v.

| Compound according to Example | ED$_{50}$ [nmol/kg] | | | |
|---|---|---|---|---|
| | 10 min. | 30 min. | 60 min. | 120 min. |
| 1 | 1.1 | 3.9 | 4.6 | 13 |
| 22 | 3 | 3.7 | 10 | 12 |
| 4 | 0.4 | 3.1 | 11.9 | 21.7 |
| 6 | 0.5 | 2.6 | 11.4 | 29 |
| 2 | 0.35 | 3.8 | 13.4 | 41 |
| 25 | 1.1 | 5.7 | 11.2 | 12.9 |
| 27 | 5.9 | 7.3 | 15.4 | 38 |
| 29 | 3.7 | 3.9 | 4.1 | 5.0 |
| 32 | 1.0 | 3.0 | 9.9 | 24 |
| 33 | 1.9 | 4.6 | 8.3 | 21 |
| 38 | 0.3 | 1.9 | 3.6 | 79 |
| 29 | 0.6 | 1.3 | 2.9 | 13.4 |
| Morphine.HCl | 17 | 19 | 21 | 37 |

TABLE 2

Haffner test in mice, ED$_{50}$ values in nmol/kg, p.o.

| Compound | ED$_{50}$ [nmol/kg] | | | |
|---|---|---|---|---|
| | 30 min. | 60 min. | 120 min. | 180 min. |
| 1 | 30 | 35 | 37 | 46 |
| 22 | 55 | 90 | 96 | 86 |
| 4 | 35 | 46 | 58 | 69 |
| 6 | 58 | 108 | 120 | 132 |
| 2 | 17 | 21 | 33 | 36 |
| 25 | 20.1 | 28 | 31 | 37 |
| 27 | 59 | 73 | 108 | 178 |
| 29 | 70 | 85 | 96 | 131 |
| 32 | 68 | 120 | 154 | 232 |
| 33 | 29 | 37 | 51 | 69 |
| 38 | 23 | 27 | 35 | 43 |
| 39 | 27 | 35 | 149 | 283 |
| Morphine.HCl | 279 | 296 | 539 | 718 |

2) 7,8-DIHYDROMORPHINE ETHERS

EXAMPLE 1

6α-((4-Acetyloxy-butyl)-oxy)-4,5-epoxy-17-methyl-morphinan-3-ol acetate

6α-((4-Acetyloxy-butyl)-oxy)-4,5α-epoxy-17-methyl-morphinan-7-en-3-ol acetate (0.288 g, 0.63 mmol) in MeOH (30 ml) mixed with 10% Pd on 0.2 g) and then agitated for 1 hour at RT under H$_2$ (1 bar over pressure). The catalyst is removed by filtering through a filter compound and the filtrate is concentrated by rotary evaporation. The residue obtained is purified by flash chromatography (20 g silica gel; mobile phase: CH$_2$Cl$_2$/MeOH=9/1). The product is dissolved in glacial acetic acid and lyophilised.

Yield: 0.20 g (0.43 mmol, 68.8%) 6α-((4-acetyloxybutoxy)oxy)-4,5α-epoxy-17-methyl-morphinan-3-ol-acetate $^{13}$C NMR (300 MHz, CDCl$_3$) δ 171.7, 145.9, 138.9, 127.9, 120.4, 119.2, 118.1, 88.8, 74.3, 69.8, 64.7, 62.2, 48.3, 41.6, 40.6, 38.0, 33.6, 26.2, 25.5, 24.7, 21.6, 21.1, 18.0.

Starting compound: see Example 1 of "Ethers" above.

The following compounds were prepared analogously to Example 1:

EXAMPLE 2

6α-[3-(Acetyloxy)propyl]oxy-4,5α-3-methoxymethyl-17-methyl-morphine

C$_{24}$H$_{33}$NO$_6$
MW: 431.53 gmol$^{-1}$ $^{13}$C NMR (100 MHz, CDCl$_3$) δ 170.7, 147.9, 139.5, 123.0, 118.7, 118.6, 95.6, 88.7, 74.1, 66.3, 61.4, 61.3, 56.2, 48.0, 41.2, 40.2, 38.5, 33.7, 28.9, 25.3, 21.3, 20.7, 17.5.

EXAMPLE 3

6α-[3-(Acetyloxy)propyl]oxy-4,5α-epoxy-17-methyl-morphin-3-ol acetate

C$_{24}$H$_{33}$NO$_7$
MW: 447.53 gmol$^{-1}$ $^{13}$C NMR (100 MHz, CDCl$_3$) δ 175.2, 17.7, 146.1, 138.9, 127.8, 120.5, 119.0, 118.4, 88.3, 74.2, 66.0, 48.1, 41.2, 40.6, 37.8, 33.8, 28.9, 24.8, 21.2, 21.0, 20.7, 17.9.

Example A

TABLE 1

Haffner test in mice, ED$_{50}$ values in nmol/kg, i.v.

| Compound according to Example | ED$_{50}$ [nmol/kg] | | | |
|---|---|---|---|---|
| | 10 min. | 30 min. | 60 min. | 120 min. |
| 1 | 1.5 | 1.9 | 3.7 | 9.1 |
| 7,8-Dihydromorphine | 16 | 23 | 32 | 130 |
| Morphine.HCl | 17 | 19 | 21 | 37 |

TABLE 2

Haffner test in mice, ED$_{50}$ values in nmol/kg, p.o.

| Compound according to Example | ED$_{50}$ [nmol/kg] | | | |
|---|---|---|---|---|
| | 30 min. | 60 min. | 120 min. | 180 min. |
| 1 | 18 | 30 | 43 | 85 |
| 7,8-Dihydromorphine | 177 | 195 | 250 | 481 |
| Morphine.HCl | 279 | 296 | 539 | 718 |

3) ETHERS CONTAINING A CYCLIC GROUP

EXAMPLE 1

4,5α-Epoxy-17-methyl-6α-((2-tetrahydropyranyl-methoxy)-morphinan-7-en-3-ol acetate 4,5α-Epoxy-3-methoxymethoxy-17-methyl-morphinan-7-en-6α-ol See Example 1 of "Ethers" above 4,5α-Epoxy-3-methoxymethoxy-17-methyl-6α-((2-tetrahydropyranyl)-methoxy)-morphinan-7-ene NaH (50% suspension in mineral oil, 1.44 mg, 60 mmol) is washed 3× with n-pentane (8 ml) and stirred with absolute dimethylformamide (24 ml) at ambient temperature. Then a solution of 4,5α-epoxy-4-methoxy-methoxy-17-methyl-morphinan-7-en-6α-ol (3.95 g, 12 mmol) in dimethylformamide (24 ml) is added. After the development of gas has ceased, a solution of 2-(bromomethyl)-tetrahydropyran (10.64 g, 60 mmol) in dimethylformamide (16 ml) is slowly added dropwise. The resulting mixture is then stirred for 2 hours at ambient temperature. The reaction mixture is poured onto water (150 ml) and extracted 3× with methylene chloride (80 ml). The methylene chloride phases are combined, dried over Na$_2$SO$_4$, filtered and concentrated by rotary evaporation. The residue thus obtained is purified by flash chromatography (90 g silica gel; mobile phase: methylene chloride/methanol=9:1). Yield: 2.17 g 4,5α-epoxy-3-methoxymethoxy-17-methyl-6α-((2-tetrahydropyranyl)-methoxy)-morphinan-7-ene (42.3%).

$^{13}$C NMR (100 MHz, CDCl$_3$) δ 148.6, 138.8, 131.0, 130.9, 128.3, 128.1, 118.9, 118.3, 118.2, 96.1, 95.9, 89.9, 89.5, 77.0, 76.9, 74.8, 72.7, 72.5, 68.3, 68.2, 58.8, 56.2, 46.3, 43.2, 42.8, 40.9, 40.7, 35.6, 28.4, 28.3, 25.9, 23.0, 20.6.

4,5α-Epoxy-17-methyl-6α-((2-tetrahydropyranyl)-methoxy)-morphinan-7-en-3-ol acetate 4,5α-Epoxy-3-methoxymethoxy-17-methyl-6α-((2-tetrahydropyranyl)-methoxy)-morphinan-7-ene (2.17 g, 5.08 mmol) is dissolved in water (65 ml) and glacial acetic acid (65 ml) and then stirred for 6 hours at 100° C. The volatile components are eliminated using the Rotavapor. The residue thus obtained is purified by flash chromatography (130 g of silica gel; mobile phase: methylene chloride/methanol=9:1). The product is dissolved in a mixture of water and glacial acetic acid and lyophilised. Yield: 1.55 g 4,5α-epoxy-17-methyl-6α-((2-tetrahydropyranyl)-methoxy)-morphinan-7-en-3-ol acetate (68.8%).

$^{13}$C NMR (100 MHz, CDCl$_3$) δ 176.2, 146.4, 139.5, 139.4, 132.0, 131.8, 129.1, 125.9, 125.5, 122.5, 122.4, 119.8, 119.7, 118.3, 118.0, 88.9, 88.4, 77.7, 77.5, 73.5, 73.2, 72.8, 72.1, 69.6, 68.3, 59.8, 59.6, 47.0, 46.7, 41.8, 41.2, 38.0, 37.8, 33.0, 28.1, 27.8, 25.7, 23.1, 23.0, 21.8, 21.6, 21.5.

The following were prepared analogously to Example 1:

EXAMPLE 2

4,3α-Epoxy-3-methoxymethoxy-17-methyl-6α-(N-morpholinyl-carbonyl-methyl-oxy)-morphinan-7-ene $^{13}$C NMR (100 MHz, CDCl$_3$) δ 167.5, 148.0, 138.7, 130.9, 129.8, 128.9, 128.5, 119.0, 117.7, 95., 88.8, 74.5, 68.7, 66.7, 66.5, 58.6, 55.9, 46.2, 43.0, 40.6, 35.5, 20.4.

EXAMPLE 3

4,5α-Epoxy-17-methyl-6α-(N-morpholinyl-carbonyl-methyl-oxy)-morphinan-7-en-3-ol acetate $^{13}$C NMR (100 MHz, CDCl$_3$) δ 176.5, 168.6, 146.3, 139.7, 130.6, 129.8, 128.3, 123.7, 120.1, 118.2, 89.5, 74.0, 68.7, 67.2, 59.4, 46.7, 46.4, 42.7, 42.6, 41.8, 39.0, 34.0, 22.4, 21.6.

EXAMPLE 4

4,5α-Epoxy-3-methoxymethoxy-17-methyl-6α-((4-(methyloxy-carbonyl)-phenyl)-methoxy)-morphinan-7-ene $^{13}$C NMR (100 MHz, CDCl$_3$) δ 166.8, 148.5, 143.7, 139.0, 131.0, 130.7, 129.6, 129.3, 128.2, 127.2, 119.2, 118.5, 96.0, 89.4, 73.6, 70.1, 59.1, 56.2, 52.0, 46.5, 43.1, 42.9, 40.6, 35.4, 20.8.

EXAMPLE 5

4,5α-Epoxy-17-methyl-6α-((4-(methyloxycarbonyl)-phenyl)-methoxy)-morphinan-7-en-3-ol acetate $^{13}$C NMR (100 MHz, CDCl$_3$) δ 176.1, 166.9, 146.1, 138.8, 130.6, 129.8, 129.7, 129.6, 127.4, 124.0, 119.7, 117.6, 89.5, 73.8, 70.7, 59.0, 52.1, 46.3, 42.9, 41.7, 39.1, 34.0, 21.8, 21.3.

EXAMPLE 6

4,5α-Epoxy-3-methoxymethoxy-17-methyl-6α-((3-(N-phthalimido)-propyl)-oxy)-morphinan-7-ene $^{13}$C NMR (100 MHz, CDCl$_3$) δ 168.2, 148.6, 138.7, 133.7, 132.1, 131.2, 130.7, 128.6, 128.3, 123.0, 118.8, 118.3, 96.0, 89.5, 74.5, 66.6, 58.7, 56.1, 46.3, 43.1, 42.9, 40.9, 35.7, 35.5, 28.8, 20.5.

EXAMPLE 7

4,5α-Epoxy-17-methyl-6α-((3-(N-phthalimido)-propyl)-oxy)-morphinan-7-en-3-ol acetate $^{13}$C NMR (100 MHz, CDCl$_3$) δ 176.3, 169.3, 146.8, 139.2, 134.3, 132.4, 132.0, 131.4, 129.9, 127.3, 124.1, 123.7, 119.8, 118.0, 89.4, 75.3, 67.1, 59.3, 46.6, 43.2, 42.0, 39.4, 36.3, 34.5, 28.9, 22.3, 21.6.

EXAMPLE 8

4,5α-Epoxy-3-methoxymethoxy-17-methyl-6α-((4-(N-phhalimido)-butyl)-oxy)-morphinan-7-ene $^{13}$C NMR (100 MHz, CDCl$_3$) δ 169.5, 161.9, 147.5, 138.8, 132.0, 128.5, 128.3, 126.0, 122.2, 119.0, 118.6, 95.0, 87.7, 72.5, 60.0, 55.37, 48.2, 38.4, 36.7, 35.8, 34.3, 30.6, 26.2, 25 .1, 24.4, 23.4, 20.1.

EXAMPLE 9

4,5α-Epoxy-17-metheyl-6α-((4-(N -phthalimido)-butyl)-oxy)-morphinan-7-en-3-ol acetate $^{13}$C NMR (100 MHz, CDCl$_3$) δ 168.5, 145.9, 138.3, 133.6, 131.8, 130.8, 129.6, 127.4, 124.4, 123.0, 119.0, 116.8, 89.2, 74.4, 68.2, 58.6, 46.0, 42.8, 41.8, 39.6, 37.4, 34.5, 29.4, 26.7, 24.7, 20.7.

EXAMPLE 10

(5α,6α)-6-[(4-Cyanophenyl)methyl]oxy-7,8-didehydro-4,5-epoxy-17-methyl-morphinan-3-ol acetate

C$_{37}$H$_{28}$N$_2$O$_5$

MW: 460.53 gmol$^{-1}$ $^{13}$CNMR(100 MHz, CDCl$_3$) δ 176.0, 146.2, 143.6, 138.4, 132.1, 130.2, 129.7, 129.3, 127.8, 125.5, 119.3, 118.7, 117.1, 111.3, 89.5, 74.3, 70.0, 58.7, 46.3, 43.4, 42.6, 40.6, 35.4, 20.6, 20.2.

EXAMPLE 11

(5α,6α)-6-[(2-Cyanophenyl)methyl]oxy-7,8-didehydro-4,5-epoxy-17-methyl-morphinan-3-ol acetate

C$_{27}$H$_{28}$N$_2$O$_5$

MW: 460.53 gmol$^{-1}$ $^{13}$C NMR (100 MHz, CDCl$_3$) δ 146.2, 141.4, 138.6, 132.9, 132.7, 130.1, 129.4, 129.2, 128.3, 125.2, 119.1, 117.3, 117.1, 111.7, 89.1, 74.9, 68.9, 58.5, 50.1, 46.2, 43.2, 42.4, 40.5, 35.3, 20.4.

EXAMPLE 12

(5α,6α)-6-[3-(Methoxycarbonyl)phenylmethyl]oxy-7,8-didehydro-4,5-epoxy-17-methyl-morphinan-3-ol acetate

C$_{28}$H$_{31}$NO$_7$

MW: 493.56 gmol$^{-1}$ $^{13}$C NMR (100 MHz, CDCl$_3$) δ 172.1, 166.3, 146.3, 139.5, 138.7, 132.6, 130.8, 130.3, 129.8, 129.4, 128.8, 128.3, 128.2, 118.6, 116.4, 88.6, 73.9, 69.5, 58.2, 52.2, 46.1, 43.0, 42.7, 40.5, 35.5, 21.2, 20.3.

EXAMPLE 13

(5α,6α)-7,8-Didehydro-4,5-epoxy-methoxymethoxy-17-methyl-6-[2-(methoxycarbonyl)phenylmethyl]oxy-morphinane

C$_{28}$H$_{31}$NO$_6$

MW: 477.56 gmol$^{-1}$ $^{13}$C NMR (100 MHz, CDCl$_3$) δ 167.4, 148.7, 141.0, 138.8, 132.2, 131.4, 130.7, 130.1, 128.8, 128.7, 127.7, 127.6, 126.7, 118.9, 118.4, 96.0, 89.6, 74.4, 68.7, 58.8, 56.1, 51.8, 46.4, 43.3, 43.0, 41.0, 35.8, 20.6.

EXAMPLE 14

(5α,6α)-7,8-Didehydro-4,5-epoxy-17-methyl-6-[2-(methoxycarbonyl)phenylmethyl]oxy-morphinan-3-ol acetate

C$_{28}$H$_{31}$NO$_7$

MW: 493.56 gmol$^{-1}$ $^1$H-NMR (CDCl$_3$) 1.8–2.6 (4H, m, 15-H$_2$ and 16-H$_2$), 2.29 (1H, dd, J$_{gem}$=18.0 and J$_{10.9}$=6.0 Hz, 10-H$_\alpha$), 2.40 (3H, s, N—CH$_3$), 2.61 (1H, m, 14-h), 3.06 (1H, d, J=18.2 Hz, 10-H$_\beta$), 3.41 (1H, q, J$_{9.10}$=6.2 Hz, 9-H), 4.09 (1H, m), 4.84 (1H, dd, J$_{5.6}$, 6=6.0 Hz and J$_{5.7}$=1.1 Hz, 5-H), 5.00 (1H, d, J=6.0 Hz), 5.31 (1H, m, 8-H), 5.72 (1H, m, 7-H), 6.38–6.58 (2H, AB system, J=8.2 Hz, 1-H and 2-H), 7.50 (2H, d, J=10.2 Hz), 8.00 2H, d, J=11.4 Hz).

EXAMPLE 15

(5α,6α)-7,8-Didehydro-4,5-epoxy-6-[[5-hydroxy-6-(hydroxymethyl)-benzylacetal-2-pyridinyl]methyl]oxy-17-methyl-morphinane

C$_{33}$H$_{34}$N$_2$O$_6$

MW: 554.65 gmol$^{-1}$ $^{13}$C NMR (100 MHz, CDCl$_3$) δ 150.9, 148.7, 148.4, 140.4, 138.7, 136.1, 131.0, 130.3, 129.3, 128.6, 128.5, 128.2, 126.1, 124.3, 121.5, 118.8, 118.2, 99.1, 95.8, 89.3, 73.7, 71.1, 68.4, 58.6, 56.0, 46.2, 43.0, 42.7, 40.7, 35.5, 20.4.

EXAMPLE 16

(5α,6α)-7,8-Didehydro-4,5-epoxy-6-[[5-hydroxy-6-(hydroxymethyl)-2-pyridinyl]methyl]oxy-17-methyl-morphinan-3-ol acetate $C_{26}H_{30}NO_7 \cdot \frac{1}{3} C_6H_{15}N$
MW: 482.54 gmol$^{-1}$+33.67 gmol$^{-1}$=516.21 gmol$^{-1}$
ES-MS m/z 423 (M+1)

EXAMPLE 17

(5α,6α(-6-[(3-Cyanophenyl)methyl]oxy-7,8-didehydro-4,5-epoxy-3-methoxymethoxy-17-methyl-morphinane $C_{27}H_{28}N_2O_4$
MW: 444.53 gmol$^{-1}$
$^{13}$C NMR (100 MHz, CDCl$_3$) δ 148.3, 140.0, 139.0, 131.6, 131.0, 130.2, 128.9, 128.4, 119.1, 118.7, 118.0, 112.4, 95.8, 89.2, 73.7, 69.3, 58.9, 56.1, 53.3, 46.4, 43.0, 42.9, 10.8, 20.5.

EXAMPLE 18

(5α,6α(-6-[(3-Cyanophenyl)methyl]oxy-7,8-didehydro-4,5-epoxy-17-methyl-morphinan-3-ol acetate $C_{27}H_{23}N_2O_5$
MW: 460.53 gmol$^{-1}$
$^1$H-NMR (DMSO) 1.6–2.3 (4H, m, 15-H$_2$ and 16-H$_2$), 2.10 (3H, s, Ac), 2.37 (1H, dd, J$_{gem}$=16.6 and J$_{10,9}$=4.4 Hz, 10-H$_α$), 2.33 (3H, s, N—CH$_3$), 2.59 (1H, m, 14-H), 2.88 (1H, d, J=17.8 Hz, 10-H$_β$), 3.30 (1H, q, J$_{9,10}$=5.6 Hz, 9-H), 4.07 (1H, m), 4.60–4.78 (2×H, 2× d, J=8.8 Hz), 5.00 (1H, d, J$_{5,6}$=6.7 Hz and J$_{5,7}$=1.2 Hz, 5-H), 5.33 (1H, m, 8-H), 5.62 (1H, m, 7-H), 6.34–6.47 (2H, AB system, J =12.4 Hz, 1-H and 2-H), 7.55 (1H, t, J=7,8 Hz), 7.55 (2H, m) 7,86 (1H, s)

EXAMPLE 19

(5α,6α)-6-[4-(2-t-Butyl-5-tetrazolyl)-phenylmethyl]oxy-7,8-didehydro-4,5-epoxy-3-methoxymethoxy-17-methyl-morphinane $C_{31}H_{37}N_5O_4$
MW: 543.67 gmol$^{-1}$
$^{13}$C NMR (100 MHz, CDCl$_3$) δ 164.3, 148.6, 140.3, 138.9, 131.2, 130.6, 128.8, 128.7, 127.9, 127.2, 126.8, 119.0, 118.3, 96.0, 89.7, 73.4, 70.3, 63.7, 58.9, 56.2, 46.2, 43.3, 43.0, 41.0, 35.8, 29.3, 20.6.

EXAMPLE 20

(5α,6α)-6-[4-(2-t-Butyl-5-tetrazolyl)-phenylmethyl]oxy-7,8-didehydro-4,5-epoxy-17-methyl-morphinan-3-ol acetate $C_{31}H_{37}N_5O_5$
MW: 559.67 gmol$^{-1}$
$^1$H-NMR (DMSO) 1.74 (9H, s, 3×CH$_3$), 1.8–2.6 (5H, m, 10-H$_α$, 15-H$_2$ and 16-H$_2$), 1.98 (3H, s, Ac), 2.33 (3H, s, N—CH$_3$), 2.56 (1H, m, 14-H), 3.00 (1H, d, J=18.6 Hz, 10-H$_β$), 3.31 (1H, q, J$_{9,10}$=6.4 Hz, 9-H), 3.99 (1H, m, 6-H), 4.65 (1H, d, J=12 Hz), 4.80 (1H, d, J=12 Hz), 5.01 (1H, d, J=6 Hz), 5.32 (1H, m), 5.66 (1H, m), 6.36 (1H, d, J=8.0 Hz), 6.42 (1H, d, J=8.0 Hz), 7.59 (2H, d, J =8.0 Hz), 8.04 (2H, d, J=8.0 Hz)

EXAMPLE 21

(5α,6α)-7,8-Didehydro-4,5-epoxy-6-[4-(hydroxymethyl)-phenylmethyl]-3-methoxymethoxy-17-methyl-morphinane $C_{27}H_{31}NO_6$
MW: 449.55 gmol$^{-1}$ $^{13}$C NMR (100 MHz, CDCl$_3$) δ 148.5, 140.7, 138.8, 137.4, 131.2, 130.7, 128.6, 127.8, 126.9, 119.0, 118.3, 96.1, 89.6, 73.1, 70.3, 64.7, 58.7, 46.3, 43.1, 42.8, 40.7, 35.5, 20.5.

EXAMPLE 22

(5α,6α)-7,8-Didehydro-4,5-epoxy-6-[4-(hydroxymethyl)-phenylmethyl]-17-methyl-morphinan-3-ol acetate $C_{27}H_{31}NO_6$
MW: 465.55 gmol$^{-1}$ $^1$H-NMR (DMSO) 1.6–2.3 (4H, m, 15-H$_2$ and 16-H$_2$), 1.89 (3H, s, Ac), 2.45 (1H, dd, J$_{gem}$=16.0 and J$_{10,9}$=4.0 Hz, 10-H$_α$), 2.54 (3H, s, N—CH$_3$), 2.59 (1H, m, 14-H), 2.88 (1H, d, J=18.6 Hz, 10-H$_β$), 3.26 (1H, q, J$_{9,10}$=5.0 Hz, 9-H), 4.01 (1H, m, 6-H), 4.48 (2H, s), 4,53–4.67 (2×H, 2×d, J=9.4 Hz), 5.00 1H, dd, J$_{5,6}$=7.0 Hz and J$_{5,7}$=1.0 Hz, 5-H), 5.33 (1H, m, 8-H), 5.63 (1H, m, 7-H), 6.33–6.45 (2H, AB system, J=12.0 Hz, 1-H and 2-H), 7.28 (2H, d, J=8.1 Hz), 7.34 (3H, d, J=8.1 Hz).

EXAMPLE 23

(5α,6α)-7,8-Didehydro-4,5-epoxy-6-[4-(ethoxycarbonyl)-phenylmethyl]oxy-3-methoxymethoxy-17-methyl-morphinan $C_{29}H_{33}NO_6$
MW: 491.59 gmol$^{-1}$ $^{13}$C NMR (100 MHz, CDCl$_3$) δ 166.4, 148.5, 143.5, 138.9, 131.2, 130.5, 129.7, 129.6, 128.9, 128.7, 128.1, 119.1, 118.3, 96.0, 89.6, 73.7, 70.1, 60.8, 58.9, 56.2, 46.4, 43.2, 43.0, 41.0, 35.8, 20.6, 14.3.

EXAMPLE 24

(5α,6α)-7,8-Didehydro-4,5-epoxy-6-[4-(ethoxycarbonyl)-phenylmethyl]oxy-17-methyl-morphinan-3-ol acetate $C_{27}H_{31}NO_6$
MW: 507.59 gmol$^{-1}$ $^1$H-NMR (DMSO) 1.31 (3H, t, J=7.3 Hz, CH$_3$), 1.8–2.6 (4H, m, 15-H$_2$ and 16-H$_2$), 1.89 (3H, s, AcOH), 2.25 (1H, dd, J$_{gem}$=18.0 and J$_{10,9}$=5.8 Hz, 10-H$_α$), 2.31 (3H, s, N—CH$_3$), 2.56 (1H, m, 14-H), 2.87 (1H, d, J=18.5 Hz, 10-H$_β$), 3.26 (1H, q, J$_{9,10}$=6.4 Hz, 9-H), 4.02 (1H, m, 6-H), 4.30 (2H, q, J=7.3 Hz, CH$_2$), 4.65–4.81 (2×1H, 2×d, 2×J= 12.7 Hz), 5.00 (1H, m, 5-H), 5.33 (1H, m), 5.65 (1H, m), 6.33–6.45 (2H, AB system, J=8.0 Hz), 7.55 (2H, d, J=8.0 Hz), 7.94 (2H, d, J=8.0 Hz).

Example A

| Haffner test in mice, ED$_{50}$ values in nmol/kg, p.o. | | | | |
|---|---|---|---|---|
| | ED$_{50}$ [nmol/kg] | | | |
| Compound | 30 min. | 60 min. | 120 min. | 180 min. |
| 5 | 60 | 68 | 72 | 90 |
| Morphine.HCl | 279 | 296 | 539 | 718 |

| Haffner test in mice, ED$_{50}$ values in nmol/kg, i.v. | | | | |
|---|---|---|---|---|
| | ED$_{50}$ [nmol/kg] | | | |
| Compound | 10 min. | 30 min. | 60 min. | 120 min. |
| 5 | 0.8 | 0.8 | 3.2 | 9.5 |
| Morphine.HCl | 17 | 19 | 21 | 37 |

4) 7,8-DIHYDROMORPHINE ETHERS CONTAINING A CYCLIC GROUP

EXAMPLE 1

4,5α-Epoxy-17-methyl-6α-((4-(methyloxycarbonyl)-phenyl)-methoxy)-morphinan-3-ol acetate 4,5α-Epoxy-3-methoxymethoxy-17-methyl-morphinan-7-en-6α-ol See Example 1 of "Ethers" above.

4,5α-Epoxy-3-methoxymethoxy-17-methyl-6α-((4-(methyloxycarbonyl)-phenyl)-methoxy)-morphinan-7-ene NaH (50% suspension in mineral oil, 1.44 mg, 60 mmol) is washed 3× with n-pentane (8 ml) and stirred with absolute dimethylformamide (24 ml) at ambient temperature. Then a solution of HN-52084 (3.95 g, 12 mmol) in dimethylformamide (24 ml) is added. After the development of gas has ceased, a solution of methyl bromo-4-tolylate (1.38 g, 6 mmol) in dimethylformamide (16 ml) is slowly added dropwise. The resulting mixture is then stirred for 2 hours at ambient temperature. The reaction mixture is poured onto water (150 ml) and extracted 3× with methylene chloride (80 ml). The methylene chloride phases are combined, dried over Na$_2$SO$_4$, filtered and concentrated by rotary evaporation. The residue thus obtained is purified by flash chromatography (90 g silica gel; mobile phase: methylene chloride/methanol=9:1). Yield: 2.12 g 4,5α-epoxy-3-methoxymethoxy-17-methyl-6α-((4-(methyloxycarbonyl)-phenyl)-methoxy)-morphinan-7-ene (74%).

4,5α-Epoxy-3-methoxymethoxy-17-methyl-6α-((4-(methyloxycarbonyl)-phenyl)-methoxy)-morphinane.

A solution of 4,5α-epoxy-3-methoxymethoxy-17-methyl-6 α-((4-(methyloxycarbonyl)-phenyl)-methoxy)-morphinan-7-ene (1.90 g, 3.98 mmol) in MeOH (70 ml) is mixed with 10% Pd/C (1.17 g) and agitated for 0.5 hours under 1 bar of H$_2$ pressure. The catalyst is removed by filtering through Celite and the filtrate is evaporated down. The residue is purified by flash chromatography (silica gel; mobile phase: dichloromethane: MeOH=3:1). Yield: 1.44 g 4,5α-epoxy-3-methoxymethoxy-17-methyl-6α-((4-(methyloxycarbonyl)-phenyl)-methoxy)-morphinane (75.4%).

$^{13}$C NMR (100 MHz, CDCl$_3$) δ 167.0, 147.7, 144.5, 139.0, 130.4, 129.3, 128.7, 127.8, 126.3, 118.5, 117.2, 95.6, 89.9, 74.7, 71.1, 59.8, 56.0, 51.9, 47.2, 42.9, 42.2, 41.8, 37.0, 26.0, 20.3, 19.0.

4,5α-Epoxy-17-methyl-6α-((4-(methyloxycarbonyl)-phenyl)-methoxy)-morphinan-3-ol acetate.

4,5α-Epoxy-3-methoxymethoxy-17-methyl-6α-((4-(methyloxycarbonyl)-phenyl)-methoxy)-morphinane (1.40 g, 2.92 mmol) is dissolved with water (35 ml) and glacial acetic acid (35 ml) and then stirred for 4 hours at 100° C. The volatile components are eliminated using the Rotavapor. The residue thus obtained is purified by flash chromatography (100 g of silica gel; mobile phase: methylene chloride/methanol= 4:1). The product is dissolved in a mixture of water and glacial acetic acid and lyophilised. Yield: 1.225 g 4,5α-epoxy-17-methyl-6α-((4-(methyloxycarbonyl)-phenyl)-methoxy)-morphinan-3-ol acetate (84.7%).

$^{13}$C NMR (100 MHz, CDCl$_3$) δ 176.7, 167.0, 145.8, 144.1, 139.4, 129.3, 128.8, 128.3, 126.4, 121.0, 118.8, 117.7, 88.9, 74.3, 60.5, 52.0, 47.3, 40.7, 38.5, 34.2, 25.6, 22.1, 21.2, 18.1.

The following compounds were prepared analagously to Example 1.

EXAMPLE 2

4,5α-Epoxy-6α-[(4'-methoxycarbonyl) phenylmethyl]oxy-17-methyl-morphine

C$_{28}$H$_{33}$NO$_7$

MW: 495.58 gmol$^{-1}$ $^{13}$CNMR(100 MHz CDCl$_3$) δ 167.0, 147.7, 144.5, 139.0, 130.4, 129.3, 128.7, 127.8, 126.3, 118.5, 117.2, 95.6, 89.9, 74.7, 71.1, 59.8, 56.0, 51.9, 47.2, 41.8, 37.0, 26.0, 20.3, 19.0.

EXAMPLE 3

4,5α-Epoxy-6α-[(4'-methoxycarbonyl) phenylmethylloxy-17-methyl-morphin-3-ol acetate

C$_{28}$H$_{33}$NO$_7$

MW: 495.58 gmol$^{-1}$ $^{13}$CNMR(100 MHz CDCl$_3$) δ 176.7, 167.0, 145.8, 144.1, 139.4, 129.3, 128.8, 128.3, 126.4, 121.0, 118.8, 117.7, 88.9, 74.3, 71.5, 60.5, 52.0, 47.3, 40.7, 38.5, 34.2, 25.6, 22.1, 21.2, 18.1.

Example A

| Haffner test in mice, ED$_{50}$ values in nmol/kg, p.o. | | | | |
|---|---|---|---|---|
| | ED$_{50}$ [nmol/kg] | | | |
| Compound | 30 min. | 60 min. | 120 min. | 180 min. |
| 1 | 55 | 73 | 87 | 103 |
| 7,8-Dihydro-morphine.AcOH | 177 | 195 | 250 | 481 |
| Morphine.HCl | 279 | 296 | 539 | 718 |

Haffner test in mice, ED$_{50}$ values in nmol/kg, i.v.

| Compound | ED$_{50}$ [nmol/kg] | | | |
|---|---|---|---|---|
| | 10 min. | 30 min. | 60 min. | 120 min. |
| 1 | 2 | 3.2 | 12 | 52 |
| 7,8-Dihydro-morphine.AcOH | 16 | 23 | 32 | 130 |
| Morphine.HCl | 17 | 19 | 21 | 37 |

5) ESTERS

EXAMPLE 1

4,5α-Epoxy-6α-((4-methoxycarbonyl -butyryl)-oxy)-3-methoxymethoxy-17-methyl-morphinan-7-ene 4,5α-Epoxy-3-methoxymethoxy-17-methyl-morphinan-7-en-6α-ol See Example 1 of "Ethers" above 4,5α-epoxy-6α-((4-methoxycarbonyl-butyryl)-oxy)-3-methoxymethoxy-17-methyl -morphinan-7-ene 4,5α-Epoxy-3-methoxymethoxy-17-methyl-morphinan-7-en-6α-ol (2.0 g, 6.1 mmol) and 4-dimethylaminopyridine (0.8 g, 6.5 mmol) were dissolved in absolute CH$_2$Cl$_2$ (20 ml) and methyl glutarate chloride (1.0 g, 6.08 mmol) were added dropwise whilst cooling with ice and the mixture was stirred for 2 hours at this temperature. The reaction mixture was poured onto water (50 ml), the organic phase was washed twice more with 30 ml of water and dried over MgSO$_4$. The solvent was evaporated off and the residue was separated off by flash chromatography (CH$_2$Cl$_2$/MeOH 9/1).

Yield: 2.2 g (78.5%) 4,5α-epoxy-6α-((4-methoxycarbonyl-butyryl)-oxy)-3-methoxymethoxy-17-methyl-morphinan-7-ene as a colourless oil $^{13}$C NMR (CDCl$_3$) δ 173.3, 172.3, 147.9, 139.0, 131.0, 129.6, 128.7, 128.4, 119.3, 118.3, 96.0, 88.1, 68.3, 59.0, 56.2, 51.5, 46.6, 43.0, 42.8, 40.7, 35.4, 33.1, 33.1, 20.5, 20.1; ES MS m/z 458.5 (M+H)$^+$; C$_{25}$H$_{31}$NO$_7$ (MW=457.54).

EXAMPLE 2

4,5-Epoxy-6α-(4-methoxycarbonyl-butyryl)-oxy)-17-methyl-morphinan-7-en-3-ol acetate A solution of 4,5α-epoxy-6α-((4-methoxycarbonyl-butyryl)-oxy)-3-methoxymethoxy-17-methyl-morphinan-7-ene (2.0 g, 4.4 mmol) in glacial acetic acid (60 ml) is mixed with water (60 ml) and refluxed for 6 hours under N$_2$. After cooling, the solvent is evaporated off and the residue is separated by flash chromatography (silica gel; mobile phase: CH$_2$Cl$_2$:MeOH=9:1). After the elimination of the solvent, the residue was dissolved in 2 ml of glacial acetic acid and 15 ml of water and freeze-dried overnight.

Yield: 0.64 g of lyophilised 4,5α-epoxy-6α-((4-methoxycarbonyl-butyryl)-oxy)-17-methyl-morphinan-7-en 3-ol acetate $^{13}$C NMR (CDCl$_3$) δ 176.2, 174.2, 172.2, 145.5, 138.8, 129.8, 128.9, 128.6, 124.7, 119.7, 117.3, 87.8, 68.2, 59.1, 51.9, 46.6, 42.6, 42.2, 39.5, 34.5, 33.1, 33.0, 22.3, 20.9, 20.5; ES MS m/z 414.5 (M+H)$^+$; C$_{23}$H$_{27}$NO$_6$ (MW=413.48+60.02).

The following were prepared analogously:

EXAMPLE 3

4,5α-Epoxy-3-methoxymethoxy-6α-((3-methoxy-propionyl)-oxy)-17-methyl-morphinan-7-ene $^{13}$C NMR (100 MHz, CDCl$_3$) δ 171.1, 148.0, 139.1, 131.2, 129.8, 129.4, 128.9, 128.5, 119.5, 118.5, 96.1, 68.6, 68.0, 59.2, 58.9, 56.4, 46.8, 43.2, 42.9, 41.4, 40.8, 36.0, 35.5, 34.9, 20.7; ES MS m/z 416.4 (M+H)$^+$; C$_{23}$H$_{29}$NO$_6$ (MW 415.49)

EXAMPLE 4

4,5α-Epoxy-6α-((methoxy-acetyl)-oxy)-3-methoxymethoxy-17-methyl-morphinan-7-ene $^{13}$C NMR (100 MHz, CDCl$_3$) δ 169.9, 148.1, 139.1, 131.0, 129.9, 128.8, 128.0, 119.5, 118.6, 118.4, 96.2, 88.0, 69.6, 68.5, 59.2, 56.2, 46.7, 43.0, 42.7, 40.7, 35.4, 20.6; C$_{22}$H$_{27}$NO$_6$ (MW 401.46).

EXAMPLE 5

4,5α-Epoxy-3-methoxymethoxy-6α-((3-methylthio-propionyl)-oxy)-17-methyl-morphinan-7-ene $^{13}$C NMR (100 MHz, CDCl$_3$) δ 171.3, 147.8, 138.9, 130.9, 129.6, 128.6, 128.2, 119.3, 118.2, 95.9, 88.0, 68.3, 59.0, 56.1, 46.53, 42.9, 42.6, 40.6, 35.3, 34.3, 28.9, 20.4, 15.3; ES MS m/z 432.5 (M+H$^+$); C$_{23}$H$_{29}$NO$_5$S (MW 431.55).

EXAMPLE 6

4,5α-Epoxy-6α-((3-methoxy-propionyl)-oxy)-17-methyl-morphinan-7-en-3-ol acetate $^{13}$C NMR (100 MHz, CDCl$_3$) δ 176.1, 170.9, 144.5, 139.2, 129.2, 128.8, 127.8, 123.3, 120.0, 117.4, 86.0, 68.5, 67.0, 59.4, 58.9, 46.9, 41.6, 40.9, 38.4, 34.6, 33.4, 22.1; 20.9; ES MS m/z 372.8 (M$^+$–59) C$_{23}$H$_{29}$NO$_7$ (MW 431.4).

EXAMPLE 7

4,5α-Epoxy-6α-((methoxy-acetyl)-oxy)-17-methyl-morphinan-7-en-3-ol acetate $^{13}$C NMR (100 MHz, CDCl$_3$) δ 176.7, 169.9, 145.6, 139.5, 129.4, 129.1, 128.2, 123.6, 120.3, 118.1, 87.2, 70.0, 67.9, 59.8, 59.6, 47.0, 41.8, 41.6, 38.4, 33.5, 22.0, 21.6; ES MS m/z 358.5 (M$^+$–59) C$_{22}$H$_{27}$NO$_7$ (MW 417.46).

EXAMPLE 8

4,5α-Epoxy-6α-((3-methylthio-propionyl)-oxy)-17-methyl-morphinan-7-en-3-ol acetate $^{13}$C NMR (100 MHz, CDCl$_3$) δ 176.5, 171.3, 145.1, 139.1, 129.3, 128.9, 128.0, 123.6, 119.8, 117.3, 87.1, 67.7, 59.1, 46.6, 41.7, 41.5, 38.5, 34.4, 33.5, 29.2, 22.2, 21.1, 15.8; C$_{23}$H$_{29}$NO$_6$ (MW 387.50).

EXAMPLE 9

4,5α-Epoxy-6α-((3,3-dimethyl-butyryl)-oxy)-17-methyl-morphinan-7-en-3-ol acetate $^{13}$C NMR (100 MHz, CDCl$_3$) δ 176.3, 171.7, 145.6, 138.6, 129.6, 129.2, 128.3, 124.4, 119.7, 117.1, 88.3, 68.0, 58.9, 47.7, 46.3, 42.6, 41.7, 39.0, 34.0, 30.8, 29.6, 22.1, 21.1,

EXAMPLE 10

4,5α-Epoxy-6α-((3,3-dimethyl-butyryl)-oxy)-3-methoxy-methoxy-morphinan-7-ene $^{13}$C NMR (100 MHz, CDCl$_3$) δ 171.3, 147.8, 138.5, 130.7, 129.2, 128.4, 128.2, 118.8, 118.2, 95.7, 88.2, 68.0, 58.6, 55.8, 47.4, 46.1, 42.7, 42.6, 40.4, 35.1, 30.3, 29.3, 20.2.

EXAMPLE 11

4,5α-Epoxy-17-methyl-6α-((2-trifluoromethyl-2-hydroxy-propionyl)-oxy)-morphinan-7-en-3-ol acetate ES MS m/z 426.5 (M+H$^+$)

EXAMPLE 12

4,5α-Epoxy-17-methyl-6α-((3-methoxycarbonyl-propionyl)-oxy)-morphinan-7-en-3-ol acetate $^{13}$C NMR (100 MHz, DMSO-d$_6$) δ 172.5, 172.1, 171.5, 145.3, 138.9, 130.4, 130.0, 128.1, 125.0, 119.0, 116.6, 87.1, 68.1, 58.3, 51.5, 46.3, 42.6, 42.1, 34.7, 28.7, 21.2, 20.1.

EXAMPLE 13

4,5α-Epoxy-17-methyl-6α-((3-ethyloxycarbonyl-acryloyl)-oxy)-morphinan-7-en-3-ol acetate $^{13}$C NMR (100 MHz, DMSO-d$_6$) δ 172.1, 154.4, 163.9, 145.3, 138.9, 133.6, 133.1, 130.4, 130.3, 127.6 125.1, 119.1, 116.6, 86.9, 69.1, 61.2, 58.3, 46.3, 42.7, 42.2, 39.1, 34.8, 21.2, 20.1, 14.0.

EXAMPLE 14

4,5α-Epoxy-17-methyl-6α-((2-methylthio-acetyl)-oxy)-morphinan-7-en-3-ol acetate $^{13}$C NMR (100 MHz, CDCl$_3$) δ 176.7, 169.5, 145.5, 139.6, 129.4, 129.2, 127.9, 123.3, 120.4, 118.0, 87.3, 68.2, 59.6, 47.0, 41.7, 41.6, 38.2, 35.4, 33.3, 22.2, 21.6, 16.5.

EXAMPLE 15

4,5α-Epoxy-3-methoxymethoxy-17-methyl-6α-((2-trifluoromethyl-2-hydroxy-propionyl)-oxy)-morphinan-7-ene ES MS m/z 470.3 (M+H$^+$)

EXAMPLE 16

4,5α-Epoxy-6α-((3-methoxycarbonyl-propionyl)-oxy)-3-methoxymethoxy-17-methyl-morphinan-7-ene $^{13}$C NMR (100 MHz, CDCl$_3$) δ 172.6, 171.7, 147.8, 139.0, 131.0, 129.6, 128.7, 128.2, 119.3, 118.3, 96.0, 88.1, 68.5, 59.0, 56.2, 51.7, 46.6, 43.0, 42.7, 40.7, 35.3, 29.0, 20.5.

EXAMPLE 17

4,5α-Epoxy-6α-((3-ethyloxycarbonyl-acryloyl)-oxy)-3-methoxymethoxy-17-methyl-morphinan-7-ene $^{13}$C NMR (100 MHz, CDCl$_3$) δ 164.8, 164.3, 147.7, 139.1, 134.3, 133.1, 130.9, 130.0, 128.6, 127.8, 119.5, 118.2, 95.9, 87.9, 69.1, 61.3, 59.1, 56.2, 46.6, 43.0, 42.8, 40.7, 35.3, 20.5, 14.1.

EXAMPLE 18

4,5α-Epoxy-3-methoxymethoxy-17-methyl-6α-((2-methylthio-acetyl)-oxy)-morphinan-7-ene $^{13}$C NMR (100 MHz, CDCl$_3$) δ 170.1, 148.2, 139.3, 131.3, 130.2, 129.0, 128.3, 119.7, 118.7, 96.3, 88.4, 69.5, 59.3, 56.5, 46.9, 43.3, 43.2, 41.0, 35.8, 35.7, 20.8, 16.6.

EXAMPLE 19

4,5α-Epoxy-6α-((5-methoxycarbonyl-valeryl)-oxy)-3-methoxymethoxy-17-methyl-morphinan-7-ene $^{13}$C NMR (100 MHz, CDCl$_3$) δ 173.7, 172.6, 147.8, 138.9, 130.97, 129.5, 128.6, 128.4, 119.2, 118.3, 95.9, 88.1, 68.2, 59.0, 56.1, 51.4, 46.5, 42.9, 42.7, 40.6, 35.3, 33.6, 24.3, 24.2, 20.5.

EXAMPLE 20

4,5α-Epoxy-6α-((5-methoxycarbonyl-valeryl)-oxy)-17-methyl-morphinan-7-en-3-ol acetate $^{13}$C NMR (100 MHz, CDCl$_3$) δ 176.6, 174.2, 172.6, 145.6, 139.2, 129.1, 127.6, 123.0, 119.5, 117.5, 87.3, 67.6, 59.0, 51.6, 46.4, 41.9, 41.3, 38.3, 33.5, 33.4, 24.2, 24.1, 22.3, 21.2.

EXAMPLE 21

4,5α-Epoxy-6α-((6-methoxycarbonyl-hexylcarbonyl)-oxy)-3-methoxymethoxy-17-methyl-morphinan-7-en-3-ol $^{13}$C NMR (100 MHz, CDCl$_3$) δ 174.3, 173.3, 148.3, 139.2, 131.4, 129.9, 129.1, 128.8, 119.6, 118.7, 96.3, 88.6, 68.5, 59.3, 56.5, 53.7, 51.7, 469.9, 43.3, 43.2, 41.1, 35.7, 34.3, 29.0, 25.0, 24.9, 20.8.

EXAMPLE 22

4,5α-Epoxy-6α-((6-methoxycarbonyl-hexylcarbonyl)-oxy)-17-methyl-morphinan-7-en-3-ol $^{13}$C NMR (100 MHz, CDCl$_3$) δ 176.0, 174.2, 172.7, 145.2, 138.6, 129.2, 128.8, 127.7, 123.6, 119.3, 116.9, 87.4, 67.3, 58.7, 51.2, 46.1, 41.8, 41.3, 38.4, 33.6, 33.4, 28.3, 24.2, 21.7, 20.8.

EXAMPLE 23

Morphine-6-O-methyl-2,3-O-diacetyl-L$_g$-tartate

C$_{28}$H$_{35}$NO$_{11}$

Salt form: Acetate

MW: 561.59 gmol$^{-1}$ $^{13}$C NMR (100 MHz, CDCl$_3$) δ 175.8, 170.6, 169.6, 166.1, 165.1, 144.1, 139.0, 128.9, 128.7, 127.8, 123.5, 120.3, 117.4, 85.8, 71.4, 70.1, 68.5, 59.3, 53.1, 46.9, 41.6, 41.0, 38.3, 33.4, 21.6, 20.8, 20.5, 20.3.

Example A

TABLE 1

| Compound according to Example | Haffner test in mice, % MPE, ED$_{50}$ values i.v. ED$_{50}$ [nmol/kg] | | | |
|---|---|---|---|---|
| | 10 min. | 30 min. | 60 min. | 120 min. |
| 11 | 5.6 | 7 | 13 | 19 |
| 20 | 3.7 | 5.1 | 11 | 15 |
| 22 | 2.5 | 3.3 | 5 | 22 |
| 2 | 3.4 | 4.2 | 9 | 12 |
| Morphine.HCl | 17 | 19 | 21 | 37 |

TABLE 2

Haffner test in mice, $ED_{50}$ values in nmol/kg, p.o.

| Compound according to | $ED_{50}$ [nmol/kg] | | | |
|---|---|---|---|---|
| Example | 30 min. | 60 min. | 120 min. | 180 min. |
| 11 | 148 | 172 | 256 | 269 |
| 20 | 118 | 120 | 170 | 234 |
| 22 | 109 | 208 | 298 | 315 |
| 2 | 126 | 128 | 148 | 175 |
| Morphine.HCl | 279 | 296 | 539 | 718 |

6) ESTERS CONTAINING A CYCLIC GROUP

EXAMPLE 1

4,5α-Epoxy-17-methyl-6α-((2-thienyl)-acetyloxy)-morphinan-7-en-3-ol acetate 4,5α-Epoxy-3-methoxymethoxy-17-methyl-morphinan-7-en-6α-ol See Example 1 of "Ethers" above 4,5α-Epoxy-3-methoxymethoxy-17-methyl-6α-((2-thienyl)-acetyloxy)-morphinan-7-ene 4,5α-Epoxy-3-methoxymethoxy-17-methyl-morphinan-7-en-6α-ol (1.98 g, 6 mmol) and thiophene-2-acetic acid (0.853 g, 6 mmol) are dissolved in $CH_2Cl_2$ (30 ml) at 25° C. Then N,N'-dicyclohexylcarbodiimide (1.24 g, 6 mmol) and 4-dimethylaminopyridine (0.73 g, 6 mmol) are added to the stirred solution. After the solution has been stirred for a further 14 hours at 25° C., the precipitate is filtered off and washed with $CH_2Cl_2$ (20 ml). The combined organic phase is washed with water (2×10 ml), dried ($Na_2SO_4$), filtered and evaporated down using a Rotavapor. The residue thus formed is purified by flash chromatography (silica gel; mobile phase: $CH_2Cl_2$:MeOH=9:1). The residue is freed from residual solvent in a high vacuum in order to obtain 4,5α-epoxy-3-methoxymethoxy-17-methyl-6α-((2-thienyl)-acetyloxy)-morphinan-7-ene (2.07 g, 76.1%) as a colourless foam.

$^{13}C$ NMR (100 MHz, $CDCl_3$) δ 169.6, 147.5, 138.6, 134.5, 130.6, 129.4, 128.4, 127.7, 126.5, 126.4, 124.6, 119.0, 118.1, 95.66, 87.7, 68.6, 58.6, 55.9, 46.2, 42.7, 42.4, 40.3, 35.0, 34.7, 20.2.

4,5α-Epoxy-17-methyl-6α-((2-thienyl)-acetyloxy)-morphinan-7-en-3-ol acetate

A solution of 4,5α-epoxy-3-methoxymethoxy-17-methyl-6α-((2-thienyl)-acetyloxy)-morphinan-7-ene (1.00 g, 2.20 mmol) in glacial acetic acid (30 ml) is mixed with (30 ml) of water and stirred for 5 hours at 100° C. under $N_2$. The solution is evaporated down using a Rotavapor. The residue obtained is purified by flash chromatography (silica gel; mobile phase: $CH_2Cl_2$:MeOH=9:1) and lyophilised in order to obtain 4,5α-epoxy-17-methyl-6α-((2-thienyl)-acetyloxy)-morphinan-7-en-3-ol acetate (0.444 g, 89.9%) as a colourless foam.

$^{13}C$ NMR (100 MHz, $CDCl_3$) δ 176.9, 170.2, 145.6, 139.6, 135.2, 129.5, 129.2, 127.6, 127.3, 127.2, 125.4, 122.9, 120.3, 117.9, 87.3, 68.3, 59.7, 46.9, 41.8, 41.3, 38.0, 35.3, 33.1, 22.0, 21.8.

The following were prepared analogously to Example 1:

EXAMPLE 2

4,5α-Epoxy-3-methoxymethoxy-17-methyl-6α-(phenyl-acetyloxy)-morphinan-7-ene $^{13}C$ NMR (100 MHz, $CDCl_3$) δ 170.7, 147.7, 138.7, 133.6, 130.7, 129.4, 129.0, 128.4, 128.2, 128.0, 126.7, 119.0, 118.1, 95.7, 87.9, 58.7, 55.9, 46.3, 42.7, 42.5, 40.6, 40.4, 35.1, 20.2; ES MS m/z 448.5 (M+H$^+$) $C_{27}H_{29}NO_5$ (MW 447.54).

EXAMPLE 3

4,5α-Epoxy-17-methyl-6α-(phenyl-acetyloxy)-morphinan-7-en-3-ol acetate $^{13}C$ NMR (100 MHz, $CDCl_3$) δ 176.44, 170.9, 145.3, 139.1, 133.9, 129.3, 129.1, 129.08, 128.6, 128.3, 127.5, 127.2, 123.2, 119.8, 117.4, 87.3, 67.9, 59.2, 46.5, 41.7, 41.2, 41.0, 38.1, 33.2, 21.9, 21.3; ES MS m/z 404.5 (M$^+$-59) $C_{27}H_{29}NO_6$ (MW 463.54).

EXAMPLE 4

4,5α-Epoxy-3-methoxymethoxy-17-methyl-6α-((4-chlorophenyl)-acetyloxy)-morphinan-7-ene $^{13}C$ NMR (100 MHz, $CDCl_3$) δ 170.2, 147.5, 138.7, 132.7, 132.0, 130.6, 130.4, 129.5, 128.4, 128.3, 127.7, 119.0, 118.0, 95.6, 87.7, 68.5, 58.7, 55.9, 46.2, 42.7, 42.4, 40.4, 39.9, 35.0, 20.2; ES MS m/z 482.9 (M+H$^+$) $C_{27}H_{28}ClNO_5$ (MW 481.98).

EXAMPLE 5

6α-((4-Chlorophenyl)-acetyloxy)-4,5α-epoxy-17-methyl-morphinan-7-en-3-ol acetate $^{13}C$ NMR (100 MHz, $CDCl_3$) δ 176.6, 170.5, 145.3, 139.2, 133.1, 132.3, 130.8, 129.1, 129.0, 128.7, 127.7, 123.1, 119.8, 117.5, 87.1, 68.0, 59.2, 46.5, 41.7, 41.3, 40.1, 38.1, 33.2, 22.1, 21.3; ES MS m/z 482.9 (M$^+$-59) $C_{27}H_{28}ClNO_6$ (MW 481.98).

EXAMPLE 6

4,5α-Epoxy-3-methoxymethoxy-17-methyl-6α-((3-pyridyl)-acetyloxy)-morphinan-7-ene $^{13}C$ NMR (100 MHz, $CDCl_3$) δ 169.8, 150.1, 148.1, 147.3, 138.6, 136.6, 130.5, 129.5, 129.3, 128.3, 123.0, 119.1, 117.9, 95.6, 87.5, 68.5, 58.7, 55.8, 46.2, 42.6, 37.6, 35.0, 20.1.

EXAMPLE 7

4,5α-Epoxy-17-methyl-6α-((3-pyridyl)-acetyloxy)-morphinan-7-en-3-ol acetate $^{13}C$ NMR (100 MHz, $CDCl_3$) δ 175.9, 169.3, 149.7, 146.8, 145.1, 139.2, 137.7, 129.8, 128.6, 127.3, 123.4, 122.1, 119.5, 117.9, 86.4, 67.8, 58.9, 46.3, 41.2, 40.8, 38.1, 37.6, 32.7, 21.3, 21.0.

EXAMPLE 8

4,5α-Epoxy-3-methoxymethoxy-17-methyl-6α-((3-thienyl)-acetyloxy)-morphinan-7-ene $^{13}C$ NMR (100 MHz, $CDCl_3$) δ 170.5, 147.9, 139.0, 133.4, 131.0, 129.7, 128.6, 128.2, 125.5, 123.0, 119.3, 118.3, 96.0, 88.2, 68.8, 59.0, 56.2, 46.6, 43.0, 42.8, 40.7, 35.6, 35.4, 20.5.

EXAMPLE 9

4,5α-Epoxy-17-methyl-6α-((3-thienyl)-acetyloxy)-morphinan-7-en-3-ol acetate $^{13}C$ NMR (100 MHz, $CDCl_3$) δ 176.6, 170.5, 145.3, 139.1, 133.4, 129.3, 128.9, 128.6, 127.9, 125.7, 123.5, 123.1, 119.8, 117.3, 87.4, 68.1, 59.1, 46.5, 41.9, 41.4, 38.4, 35.5, 33.5, 22.1, 21.2.

EXAMPLE 10

6α-((2-Chlorophenyl)-acetyloxy)-4,5α-epoxy-3-methoxymethoxy-17-methyl-morphinan-7-ene $^{13}$C NMR (100 MHz, CDCl$_3$) δ 169.7, 147.6, 138.6, 134.3, 132.0, 131.2, 130.7, 129.4, 129.1, 128.4, 128.3, 127.9, 126.5, 119.0, 118.1, 95.7, 87.9, 68.6, 58.7, 55.9, 46.2, 42.7, 42.5, 40.4, 38.3, 35.1, 20.2.

EXAMPLE 11

6α-((2-Chlorophenyl)-acetyloxy)-4,5α-epoxy-17-methyl-morphinan-7-en-3-ol acetate $^{13}$C NMR (100 MHz, CDCl$_3$) δ 176.6, 170.0, 145.4, 139.4, 134.5, 132.2, 131.7, 129.4, 129.3, 128.9, 128.7, 127.2, 126.9, 122.7, 119.8, 117.5, 87.2, 67.9, 59.3, 46.6, 41.6, 41.3., 38.6, 37.8, 33.0, 21.9, 21.4.

EXAMPLE 12

6α-((3-Chlorophenyl)-acetyloxy)-4,5α-epoxy-3-methoxymethoxy-17-methyl-morphinan-7-ene $^{13}$C NMR (100 MHz, CDCl$_3$) δ 170.4, 147.8, 139.0, 135.7, 134.2, 130.9, 129.8, 129.7, 129.5, 128.7, 127.6, 127.3, 119.3, 118.3, 95.9, 87.9, 68.8, 59.0, 56.2, 46.6, 43.0, 42.7, 40.7, 40.4, 35.3, 20.5.

EXAMPLE 13

6α-((3-Chlorophenyl)-acetyloxy)-4,5α-epoxy-17-methyl-morphinan-7-en-3-ol acetate $^{13}$C NMR (100 MHz, CDCl$_3$) δ 176.4, 170.0, 145.0, 138.9, 135.4, 133.9, 129.4, 129.2, 128.8, 128.6, 127.5, 127.3, 127.0, 122.9, 119.5, 117.2, 86.8, 67.7, 58.8, 46.2, 41.4, 41.0, 40.0, 37.9, 33.0, 21.9, 20.9.

EXAMPLE 14

4,5α-Epoxy-3-methoxymethoxy-6α-(3-(2-methoxyphenyl)-propionyloxy)17-methyl-morphinan-7-ene $^{13}$C NMR (100 MHz, CDCl$_3$) δ 173.0, 157.7, 148.2, 139.1, 131.3, 130.4, 130.2, 129.7, 129.0, 128.9, 128.7, 127.8, 120.6, 119.5, 118.6, 110.4, 96.2, 88.6, 68.5, 59.2, 56.4, 55.3, 46.8, 43.2, 40.9, 35.6, 34.2, 26.2, 20.7.

EXAMPLE 15

4,5α-Epoxy-6α-(3-(2-methoxyphenyl)-propionyloxy)-17-methyl-morphinan-7-en-3-ol acetate $^{13}$C NMR (100 MHz, CDCl$_3$) δ 176.4, 172.7, 157.5, 145.3, 139.1, 130.0, 129.5, 129.1, 128.8, 127.6, 127.3, 123.1, 120.5, 119.8, 117.4, 110.4, 87.5, 67.4, 59.2, 55.3, 46.5, 41.8, 41.2, 38.0, 33.9, 33.1, 25.9, 21.8, 21.4.

EXAMPLE 16

4,5α-Epoxy-3-methoxymethoxy-6α-(3-(4-methoxyphenyl)-propionyloxy)-17-methyl-morphinan-7-ene $^{13}$C NMR (100 MHz, CDCl$_3$) δ 171.9, 157.6, 147.4, 138.5, 132.2, 130.6, 129.2, 128.8, 128.3, 128.0, 118.9, 117.8m 113.5, 95.5, 87.8, 67.8, 58.6, 55.8, 54.8, 46.2, 42.6, 42.3, 40.3, 35.5, 35.0, 29.6, 20.0.

EXAMPLE 17

4,5α-Epoxy-6α-(3-(4-methoxyphenyl)-propionyloxy)-17-methyl-morphinan-7-en-3-ol acetate $^{13}$C NMR (100 MHz, CDCl$_3$) δ 176.8, 172.7, 158.4, 145.7, 139.4, 132.9, 129.6, 129.5, 127.8, 123.5, 120.1, 117.7, 114.3, 87.8, 67.8, 59.5, 55.6, 46.8, 42.1, 41.6, 38.5, 36.1, 33.5, 30.3, 22.2, 21.6.

EXAMPLE 18

4,5α-Epoxy-3-methoxymethoxy-6α-(4-(4-methoxyphenyl)-butyryloxy)-17-methyl-morphinan-7-ene $^{13}$C NMR (100 MHz, CDCl$_3$) δ 173.1, 158.1, 148.2, 139.2, 133.7, 131.2, 129.6, 128.9, 128.7, 119.6, 118.6, 114.0, 96.1, 88.5, 68.5, 59.2, 56.3, 55.4, 50.7, 46.8, 43.2, 43.0, 40.9, 35.6, 34.4, 33.6, 26.9, 20.7.

EXAMPLE 19

4,5α-Epoxy-6α-(4-(4-methoxyphenyl)-butyryloxy)-17-methyl-morphinan-7-en-3-ol acetate $^{13}$C NMR (100 MHz, CDCl$_3$) δ 176.0, 172.6, 157.6, 145.1, 138.4, 133.1, 129.1, 128.7, 127.8, 123.8, 119.4, 116.9, 113.6, 87.6, 67.5, 58.7, 54.9, 46.1, 41.3, 38.4, 33.8, 33.0, 26.3, 21.7, 20.8.

EXAMPLE 20

6α-(Cyclohexylacetyloxy)-4,5α-epoxy-3-methoxymethoxy-17-methyl-morphinan-7-ene $^{13}$C NMR (100 MHz, CDCl$_3$) δ 172.1, 147.7, 138.5, 130.7, 129.2, 128.4, 128.2, 118.8, 118.1, 95.6, 93.2, 88.1, 67.9, 58.6, 55.8, 46.2, 42.7, 41.5, 40.4, 35.1, 34.4, 32.7, 25.7, 20.2.

EXAMPLE 21

6α-(Cyclohexylacetyloxy)-4,5α-epoxy-17-methyl-morphinan-7-en-3-ol acetate $^{13}$C NMR (100 MHz, CDCl$_3$) δ 176.5, 172.5, 145.5, 139.1, 129.5, 129.1, 127.4, 123.2, 119.7, 117.4, 87.8, 67.6, 59.1, 46.5, 42.0, 41.8, 41.2, 38.2, 34.7, 33.3, 33.0, 26.1, 26.0, 21.9, 21.4.

EXAMPLE 22

4,5α-Epoxy-3-methoxymethoxy-6α-((2-methoxyphenyl)-acetyloxy)-17-methyl-morphinan-7-ene $^{13}$C NMR (100 MHz, CDCl$_3$) δ 171.5, 157.8, 148.4, 139.1, 131.4, 131.1, 129.7, 129.1, 128.7, 123.2, 120.7, 119.5, 118.9, 110.8, 96.3, 88.7, 68.9, 59.2, 56.5, 55.6, 46.8, 43.2, 41.0, 35.6, 20.8.

EXAMPLE 23

4,5α-Epoxy-6α-((2-methoxyphenyl)-acetyloxy)-17-methyl-morphinan-17-en-3-ol acetate $^{13}$C NMR (100 MHz, CDCl$_3$) δ 176.7, 171.0, 157.5, 145.4, 139.3, 131.0, 129.3, 129.1, 128.6, 127.4, 122.9, 122.8, 12 0.6, 119.7, 117.4, 110.8, 87.2, 67.5, 59.2, 55.7, 46.5, 41.6, 41.2, 38.1, 35.3, 33.1, 22.3, 21.2.

EXAMPLE 24

4,5α-Epoxy-3-methoxymethoxy-6α-((3-methoxyphenyl)-acetyloxy)-17-methyl-morphinan-7-ene $^{13}$C NMR (100 MHz, CDCl$_3$) δ 170.7, 159.6, 147.8, 138.8, 135.2, 130.9, 129.6, 129.3, 128.6, 128.1, 121.6, 119.2, 118.3, 114.9, 112.6, 95.9, 88.1, 68 .6, 5 8.9, 5 6.1, 55.0, 46.4, 42.9, 42.7, 40.8, 40.6, 35.3, 20.4.

EXAMPLE 25

4,5α-Epoxy-6α-((3-methoxyphenyl)-acetyloxy)-17-methyl-morphinan-7-en-3-ol acetate $^{13}$C NMR (100 MHz, CDCl$_3$) δ 176.5, 170.7, 159.5, 145.4, 139.0, 135.3, 129.5, 129.2, 128.9, 128.0, 123.6, 121.7, 119.7, 115.5, 112.1, 87.5, 68.2, 59.0, 55.2, 46.4, 42.1, 41.5, 41.0, 38.5, 33.5, 22.2, 21.2.

EXAMPLE 26

4,5α-Epoxy-3-methoxymethoxy-6α-((4-methoxyphenyl)-acetyloxy)-17-methyl-morphinan-7-ene $^{13}$C NMR (100 MHz, CDCl$_3$) δ 171.2, 158.6, 147.8, 138.8, 130.3, 129.5, 128.7, 128.2, 125.9, 119.2, 118.3, 113.9, 95.9, 88.1, 68.6, 58.9, 56.1, 55.1, 46.4, 42.9, 42.7, 40.6, 39.9, 35.4, 20.4.

EXAMPLE 27

4,5α-Epoxy-6α-((4-methoxyphenyl)-acetyloxy)-17-methyl-morphinan-7-en-3-ol acetate $^{13}$C NMR (100 MHz, CDCl$_3$) δ 177.0 171.5, 159.0, 145.7, 139.5, 130.7, 129.5, 129.4, 128.1, 126.2, 123.7, 120.0, 117.7, 114.3, 87.6, 68.2, 59.4, 55.5, 46.8, 42.2, 41.7, 40.3, 38.7, 33.7, 22.6, 21.5.

EXAMPLE 28

4,5α-Epoxy-17-methyl-6α-((2-nitrophenyl)-acetyloxy)-morphinan-7-en-3-ol acetate

EXAMPLE 29

4,5α-Epoxy-17-methyl-6α-((3-nitrophenyl)-acetyloxy)-morphinan-7-en-3-ol acetate

EXAMPLE 30

4,5α-Epoxy-17-methyl-6α-((4-nitrophenyl)-acetyloxy)-morphinan-7-en-3-ol acetate

EXAMPLE 31

6α-((3-Cyanobenzoyl)oxy)-4,5α-epoxy-17-methyl-morphinan-7-en-3-ol acetate

EXAMPLE 32

6α-(4-Cyanobenzoyl)-oxy)-4,5α-epoxy-17-methyl-morphinan-7-en-3-ol acetate

Example A

| Haffner test in mice, ED$_{50}$ values in nmol/kg i.v. | | | | |
|---|---|---|---|---|
| | ED$_{50}$ [nmol/kg] | | | |
| Compound | 10 min. | 30 min. | 60 min. | 120 min. |
| 19 | 2 | 2.5 | 3.3 | 5.6 |
| Morphine.HCl | 17 | 19 | 21 | 37 |

| Haffner test in mice, ED$_{50}$ values in nmol/kg p.o. | | | | |
|---|---|---|---|---|
| | ED$_{50}$ [nmol/kg] | | | |
| Compound | 30 min. | 60 min. | 120 min. | 180 min. |
| 19 | 84 | 107 | 128 | 178 |
| Morphine.HCl | 279 | 296 | 539 | 718 |

7) 7,8-DIHYDROMORPHINE ESTERS

EXAMPLE 1

4,5α-Epoxy-6α-(methoxyacetyl)-oxy)-3-methoxymethoxy-17-5 methyl-morphinane 4,5α-Epoxy-6α-(methoxyacetyl)-oxy)-3-methoxymethoxy-17-methyl-morphinan-7-ene (0.59 g. 1.47 mmol) is dissolved in MeOH (30 ml), mixed with 10% Pd/C (0.47 g) and then agitated for 2 hours at ambient temperature under H$_2$ (1 bar over pressure). The catalyst is eliminated by filtering through a filter compound and the filtrate is concentrated by rotary concentration.

Yield: 0.511 g (1.27 mmol, 86.2%)

$^{13}$C NMR (100 MHz CDCl$_3$) δ 169.2, 147.5, 138.4, 129.3, 127.3, 119.0, 118.7, 95.9, 86.8, 69.0, 68.2, 59.6, 59.0, 56.1, 46.9, 42.3, 41.7, 40.6, 35.9, 25.8, 20.3, 18.8.

Preparation of the starting compound:

4,5α-Epoxy-3-methoxymethoxy-17-methyl-morphinan-7-en-6α-ol

See Example 1 of "Ethers" above 4,5α-epoxy-6α-((methoxyacetyl)-oxy)-3-methoxymethoxy-17-methyl-morphinan-7-ene 4,5α-Epoxy-3-methoxymethoxy-17-methyl-morphinan-7-en-6α-ol (2.0 g, 6.1 mmol) and 4-dimethylaminopyridine (0.8 g, 6.5 mmol) were dissolved in absolute $CH_2Cl_2$ (20 ml) and methoxy acetic acid (6.1 mmol) was added dropwise whilst cooling with ice and the resulting mixture was stirred for 2 hours at this temperature. The reaction mixture was poured onto water (50 ml), the organic phase was washed twice more with 30 ml of water and dried over $MgSO_4$. The solvent was evaporated off and the residue separated by flash chromatography ($CH_2Cl_2$/MeOH 9/1).

Yield: 2.4 g (99.6%).

EXAMPLE 2

4,5α-Epoxy-6α-(methoxyacetyl-oxy)-17-methyl-morphinan-3-ol acetate 4,5α-epoxy-6α-(methoxyacetyl-oxy-17-methyl-morphinan (0.511 g 1.27 mmol) was mixed with $H_2O$ and glacial acetic acid 20 ml and stirred for 6 hours at 100° C. The mixture was then concentrated at 40° C. using a motor vapour and the residue obtained was purified by flash chromatography (90 g silica gel; $CH_2Cl_2$/MeOH=9/1). The product was dissolved in $H_2O$ (6 ml) and glacial acetic acid (0.6 ml) and lyophilised.

Yield: 0.33 g (0.79 mmol, 62.12%)

$^{13}C$ NMR (100 MHz, $CDCl_3$) δ 175.9, 169.2, 145.1, 138.8, 127.2, 121.0, 119.3, 117.9, 86.1, 68.8, 67.4, 60.3, 58.9, 47.3, 40.7, 40.5, 38.5, 33.5, 26.1, 21.5, 20.9, 17.9.

EXAMPLE 3

4,5α-Epoxy-6α-((5-methoxycarbonyl-valeryl)-oxy)-3-methoxymethoxy-17-methyl-morphinane 4,5α-epoxy-6α-((5-methoxycarbonyl-valeryl)-oxy)-3-methoxymethoxy-17-methyl-morphinan-7-ene (0.48 g, 1.02 mmol) was dissolved in MeOH (30 ml), mixed with 10% Pd on 0.35 g of activated charcoal and then agitated for 2 hours at ambient temperature under $H_2$ (1 bar over pressure). The catalyst was illuminated by filtering through a filter compound and the filtrate was concentrated by rotary evaporation.

Yield: 0.43 g (0.91 mmol, 89.2%).

$^{13}C$ NMR (100 MHz, $CDCl_3$) δ 173.6, 171.9, 147.7, 138.9, 129.0, 126.1, 119.1, 119.0, 95.9, 86.9, 67.6, 60.3, 56.2, 51.3, 47.4, 42.0, 41.3, 39.9, 35.2, 33.5, 33.4, 25.9, 24.1, 23.8, 20.8, 18.6.

The starting compound was prepared using the method described in Example 1.

EXAMPLE 4

4,5α-Epoxy-6α-((5-methoxycarbonyl-valeryl)-oxy)-17-methyl-morphinan-3-ol acetate 4,5α-epoxy-6α-((5-methoxycarbonyl-valeryl)-oxy)-3-methoxymethoxy-17-methyl-morphinane (0.43 g, 0.91 mmol) was mixed with $H_2O$ (15 ml) and glacial acetic acid (15 ml) and stirred for 6 hours at 100° C. The mixture was then evaporated down at 40° C. using a Rotavapor and the residue obtained was purified by flash chromatography (60 g silical gel; $CH_2Cl_2$/MeOH=9/1). The product was dissolved in $H_2O$ (6 ml) and glacial acetic acid (0.6 ml) and lyophilised. Yield: 0.221 g (0.45 mmol, 49.7%).

$^{13}C$ NMR (100 MHz, $CDCl_3$) δ 174.3, 172.3, 145.4, 139.2, 127.3, 120.7, 119.5, 118.2, 86.6, 67.2, 61.4, 51.6, 48.1, 41.2, 40.6, 38.5, 33.6, 33.5, 29.6, 26.1, 24.2, 23.8, 21.4, 18.1.

Example A

TABLE 1

Haffner test in mice, $ED_{50}$ values in nmol/kg, p.o.

| Compound | $ED_{50}$ [nmol/kg] | | | |
| --- | --- | --- | --- | --- |
|  | 30 min. | 60 min. | 120 min. | 180 min. |
| 2 | 55 | 71 | 89 | 207 |
| 4 | 39 | 44 | 73 | 189 |
| 7,8-Dihydro-morphine.AcOH | 177 | 195 | 250 | 481 |
| Morphine.HCl | 279 | 296 | 539 | 718 |

8) 7,8-DIHYDROMORPHINE ESTERS CONTAINING A CYCLIC GROUP

EXAMPLE 1

4,5α-Epoxy-6α-(4-(4-methoxyphenyl)-butyryloxy)-17-methyl-morphinan-3-ol acetate 4,5α-Epoxy-3-methoxymethoxy-17-methyl-morphinan-7-en-6α-ol See Example 1 of "Ethers" above 4,5α-Epoxy-3-methoxymethoxy-6α-(4-(4-methoxyphenyl)-butyryloxy)-17-methyl-morphinan-7-ene 4,5α-Epoxy-3-methoxymethoxy-17-methyl-morphinan-7-en-6α-ol (2.64 g, 8 mmol) and 4-(4-methoxyphenyl)-butyric acid (1.55 g, 8 mmol) are dissolved in $CH_2Cl_2$ (30 ml) at 25° C. Then N,N'-dicyclohexylcarbodiimide (1.65 g, 8 mmol) and 4-dimethylaminopyridine (0.97 g, 8 mmol) are added to the stirred solution. After the solution has been stirred for a further 14 hours at 25° C. the precipitate is filtered oft and washed with $CH_2Cl_2$ (20 ml). The combined organic phase is washed with water (2×10 ml), dried ($Na_2SO_4$), filtered and concentrated in the Rotavapor. The residue thus obtained is purified by flash chromatography (silica gel; mobile phase: $CH_2Cl_2$:MeOH=9:1). The residue is freed from residual solvent under high vacuum in order to obtain 4,5α-epoxy-3-methoxymethoxy-6α-(4-(4-methoxyphenyl)-butyryloxy)-17-methyl-morphinan-7-ene (3.71 g, 91.7%)

4,5α-Epoxy-3-methoxymethoxy-6α-(4-(4-methoxyphenyl)-butyryloxy)-17-methyl-morphinane A solution of 4,5α-epoxy-3-methoxymethoxy-6α-(4-(4-methoxyphenyl)-butyryloxy)-17-methyl-morphinan-7-ene (1.01 g, 2 mmol) in MeOH (40 ml) is mixed with 10% Pd/C (650 mg) and agitated for 1.5 hours under 1 bar of $H_2$ pressure. The catalyst is removed by filtering through Celite and the filtrate is evaporated down. The residue is pure 4,5α-epoxy-3-methoxymethoxy-6α-(4-(4-methoxyphenyl)-butyryloxy)-17-methyl-morphinane (0.87 g, 85.7%).

$^{13}C$ NMR (100 MHz, $CDCl_3$) δ 172.7, 158.2, 148.2, 139.0, 134.0, 129.6, 119.3, 118.9, 114.1, 96.4, 87.7, 68.4, 60.2, 56.6, 55.6, 47.5, 43.0, 42.4, 41.1, 36.7, 34.5, 33.8, 26.6, 25.9, 20.7, 19.5;

4,5α-Epoxy-6α-(4-(4-methoxyphenyl)-butyryloxy)-17-methyl-morphinan-3-ol acetate 4,5α-Epoxy-3-methoxymethoxy-6α-(4-(4-methoxyphenyl)-butyryloxy)-17-methyl-morphinane (0.85 g, 1.67 mmol) is dissolved in water (35 ml) and glacial acetic acid (35 ml) and then stirred for 4 hours at 100° C. The volatile components are eliminated using a Rotavapor. The residue thus obtained is purified by flash chromatography (100 g silica gel; mobile phase: methylene chloride/methanol=7:1). The product is dissolved in a mixture of water and glacial acetic acid and lyophilised.

Yield: 0.51 g 4,5α-epoxy-6α-(4-(4-methoxyphenyl)-butyryloxy)-17-methyl-morphinan-3-ol acetate (58.0%)

$^{13}$C NMR (100 MHz, CDCl$_3$) δ 176.0, 172.6, 157.9, 145.2, 138.3, 133.6, 129.3, 128.3, 123.3, 119.4, 117.3, 113.8, 87.4, 67.6, 59.8, 55.3, 47.1, 41.4, 39.6, 34.9, 34.1, 33.4, 26.2, 21.9, 20.8, 18.6.

The following compounds were prepared analogously:

EXAMPLE 2

4,5α-Epoxy-3-methoxymethoxy-6α-[4'-(4"-methoxyphenyl)-propylcarbonyl]oxy-17-methyl-morphine $C_{30}H_{37}NO_6$
MW: 507.63 gmol$^{-1}$ $^{13}$C NMR (100 MHz, CDCl$_3$) δ 172.4, 157.9, 147.8, 138.7, 133.6, 129.3, 119.0, 118.6, 113.7, 96.0, 87.4, 68.1, 59.8, 56.3, 55.3, 47.1, 42.7, 40.8, 36.4, 34.2, 33.5, 26.3, 25.6, 20.4, 19.2.

EXAMPLE 3

4,5α-Epoxy-6α-[4'-(4"-Methoxyphenyl)propyl-carbonyl]oxy-17-methyl-morphin-3-ol acetate $C_{28}H_{33}NO_5 \cdot AcOH = C_{30}H_{37}NO_7$
MW: 523.63 gmol$^{-1}$ $^{13}$C NMR (100 MHz, CDCl$_3$) δ 176.0, 172.6, 157.9, 145.2, 138.3, 133.6, 129.3, 128.0, 123.3, 119.4, 117.3, 113.8, 87.4, 67.6, 59.8, 55.3, 47.1, 41.4, 39.6, 34.9, 34.1, 33.4, 26.2, 26.1, 21.9, 20.9, 18.6.

Example A

Haffner test in mice, ED$_{50}$ values in nmol/kg i.v.

| Compound | ED$_{50}$ [nmol/kg] | | | |
|---|---|---|---|---|
| | 10 min. | 30 min. | 60 min. | 120 min. |
| 1 | 2.7 | 3.2 | 3.6 | 9 |
| 7,8-Dihydro-morphine.AcOH | 16 | 23 | 32 | 130 |
| Morphine.HCl | 17 | 19 | 21 | 37 |

Haffner test in mice, ED$_{50}$ values in nmol/kg p.o.

| Compound | ED$_{50}$ [nmol/kg] | | | |
|---|---|---|---|---|
| | 30 min. | 60 min. | 120 min. | 180 min. |
| 1 | 65 | 74 | 136 | 195 |
| 7,8-Dihydro-morphine.AcOH | 177 | 195 | 250 | 481 |
| Morphine.HCl | 279 | 296 | 539 | 718 |

9) CARBAMATES

EXAMPLE 1

4,5α-Epoxy-6α-((N-ethyloxycarbonylmethyl-carbamoyl)-oxy)-3-methoxymethoxy-17-methyl-morphinan-7-ene 4,5α-Epoxy-3-methoxymethoxy-17-methyl-morphinan-7-en-6α-ol (5.27 g, 16 mmol) is dissolved in absolute DMF (16 ml) and mixed with ethylisocyanato acetate (10.33 g, 80 mmol) with stirring. After 5 hours the reaction mixture is poured onto water (150 ml) and extracted 3× with methylene chloride (50 ml). The combined organic phases are dried over sodium sulphate and filtered and the filtrate is evaporated down in a Rotavapor. The residue thus obtained is purified by flash chromatography (silica gel; methylene chloride:methanol =9:1).

Yield: (6.68 g, 91%) 4,5α-epoxy-6α-((N-ethyloxycarbonyl-methylcarbamoyl)-oxy)-3-methoxymethoxy-17-methyl-morphinan-7-ene $^{13}$C NMR (100 MHz, CDCl$_3$) δ 169.0, 161.7, 155.0, 147.1, 137.9, 130.4, 129.7, 128.6, 128.4, 127.9, 118.4, 117.7, 95.1, 88.3, 70.0, 68.1, 60.5, 58.1, 55.4, 45.7, 42.18, 42.0, 39.9, 34.5, 19.8.

Starting compound: see Example 1 of "Ethers" above

EXAMPLE 2

4,5-Epoxy-6α-((N-ethyloxycarbonylmethyl-carbamoyl)-oxy)-17-methyl-morphinan-7-en-3-ol acetate 4,5α-Epoxy-6α-((N-ethyloxycarbonylmethyl-carbamoyl)oxy)-3-methoxymethoxy-17-methyl-morphinan-7-ene (2 g, 4.36 mmol) is dissolved in water (60 ml) and glacial acetic acid (60 ml) and then stirred for 6 hours at 100° C. The volatile constituents are eliminated using a Rotavapor. The residue thus obtained is purified by flash chromatography (90 g silica gel; mobile phase: methylene chloride/methanol=9:1).

Yield: (0.95 g, 46%) 4,5α-epoxy-6α-((N-ethyloxy-carbonylmethylcarbamoyl)-oxy)-17-methyl-morphinan-7-en-3-ol $^{13}$C NMR (100 MHz, CDCl$_3$) δ 176.0, 171.3, 156.0, 138.6, 129.1, 128.5, 127.9, 123.5, 119.6, 116.8, 87.2, 66.9, 61.7, 59.0, 46.6, 42.2, 42.5, 40.9, 38.5, 33.4, 21.9, 20.5, 13.7.

The following were prepared analogously:

EXAMPLE 3

4,5α-Epoxy-6α-((N-ethyloxycarbonylethyl-carbamoyl)-oxy)-17-methyl-morphinan-7-en-3-ol acetate

EXAMPLE 4

4,5α-Epoxy-6α-(N-hydroxyethyl-carbamoyl)-oxy)-17-methyl-morphinan-7-en-3-ol acetate Example A

TABLE 1

Haffner test in mice, ED$_{50}$ values in nmol/kg, p.o.

| Compound according to Example | ED$_{50}$ [nmol/kg] | | | |
|---|---|---|---|---|
| | 30 min. | 60 min. | 120 min. | 180 min. |
| 2 | 77 | 91 | 106 | 147 |
| Morphine.HCl | 279 | 296 | 539 | 718 |

10) 7,8-DIHYDROMORPHINE CARBAMATES

EXAMPLE 1

4,5α-Epoxy-6α-((N-ethyloxycarbonylmethyl-carbamoyl)-oxy)-3-methoxymethoxy-17-methyl-morphinane A solution of 4,5α-epoxy-6α-((N-ethyloxycarbonylmethyl-carbamoyl)-oxy)-3- methoxymethoxy-17-methyl-morphinan-7-ene (1.15 g, 2.5 mmol) in methanol (50 ml) is hydrogenated with 10% Pd on activated charcoal (800 mg) at RT under 1 bar of hydrogen for 2 hours. After the reaction time has expired the resulting mixture is filtered through a filter compound, washed with methanol and concentrated by rotary evaporation.

Yield: 4,5α-epoxy-6α-((N-ethyloxycarbonylmethyl-carbamoyl)-oxy)-3-methoxymethoxy-17-methyl-morphinane (1.00 g, 86.9%).

$^{13}$C NMR (100 MHz, CDCl$_3$) δ 170.2, 156.0, 148.3, 138.4, 130.3, 128.6, 119.4, 119.2, 96.1, 88.2, 69.9, 61.5, 60.1, 59.9, 56.4, 50.8, 47.2, 43.0, 42.5, 41.0, 36.9, 25.7, 20.6, 19.4, 14.4.

Starting compound: see Example 1 of "Carbamates" above

EXAMPLE 2

4,5α-Epoxy-6α-((N-ethyloxycarbonylmethyl-carbamoyl)-oxy)-17-methyl-morphinan-3-ol acetate 4,5α-Epoxy-6α-((N-ethyloxycarbonylmethyl-carbamoyl)-oxy)-3-methoxymethoxy-17-methyl-morphinane (0.9994 g, 2.17 mnol) is dissolved in H$_2$O (30 ml) and glacial acetic acid (30 ml) and stirred for 6 hours at 100° C. The reaction solution is concentrated in a Rotavapor at 40° C. The residue is purified by flash chromatography (90 g silica gel, mobile phase=CH$_2$Cl$_2$/MeOH=9/1).

Yield: 4,5α-Epoxy-6α-((N-ethyloxycarbonylmethyl-carbamoyl)-oxy)-17-methyl-morphinan-3-ol acetate (805 mg, 77.9%)

$^{13}$C NMR (100 MHz, CDCl$_3$) δ 176.4, 170.9, 155.9, 145.7, 138.8, 128.0, 122.2, 119.5, 118.5, 87.3, 68.6, 61.8, 60.1, 47.2, 42.8, 41.0, 39.0, 34.2, 26.4, 22.1, 21.1, 18.6, 14.1.

The following compound was prepared analogously:

EXAMPLE 3

4,5α-Epoxy-6α-((N-ethyloxycarbonylethyl-carbamoyl)-oxy)-17-methyl-morphinan-3-ol acetate
Example A

TABLE 1

Haffner test in mice, ED$_{50}$ values in nmol/kg, p.o.

| Compound | ED$_{50}$ [nmol/kg] | | | |
|---|---|---|---|---|
| | 30 min. | 60 min. | 120 min. | 180 min. |
| 2 | 24 | 33 | 52 | 118 |
| 7,8-Dihydro-morphine.AcOH | 177 | 195 | 250 | 481 |
| Morphine.HCl | 279 | 296 | 539 | 718 |

11) FURTHER ETHERS CONTAINING A CYCLIC GROUP

EXAMPLE 1

4,5α-Epoxy-17-methyl-6α-((2-pyridyl)-oxy)-morphinan-7-en-3-ol acetate 4,5α-Epoxy-3-methoxymethoxy-17-methyl-morphinan-7-en-6α-ol See Example 1 of "Ethers" above.

4,5α-Epoxy-3-methoxymethoxy-17-methyl-6α-((2-pyridyl)-oxy)-morphinan-7-ene

NaH (0.432 g, 18 mmol) is stirred with absolute DMF (12 ml) at ambient temperature and then 4,5α-epoxy-3-methoxymethoxy-17-methyl-morphinan-7-en-6α-ol (1.9764 g, 6 mmol) in DMF (12 ml) is added. After the development of gas has ceased, a solution of 2-bromopyridine in absolute DMF (8 ml) is added at RT. After 3 hours at RT this reaction mixture is poured onto H$_2$O (100 ml) and extracted 3 times with CH$_2$Cl$_2$ (60 ml). The combined organic phases are dried with Ha$_2$SO$_4$, concentrated by rotary evaporation and the residue is purified by flash chromatography (90 g silica gel, CH$_2$Cl$_2$/MeOH=9/1).

Yield: 1.00 g (2.46 mmol, 41%).

$^{13}$C NMR (100 MHz, CDCl$_3$) δ 162.7, 148.3, 146.6, 138.6, 131.4, 130.0, 128.9, 119.0, 118.9, 118.6, 117.0, 111.5, 96.1, 96.0, 89.2, 69.0, 59.1, 56.2, 46.6, 43.1, 40.8, 35.5, 20.6.

4,5α-Epoxy-17-methyl-6α-((2-pyridyl)-oxy)-morphinan-7-en-3-ol acetate 4,5α-Epoxy-3-methoxymethoxy-17-methyl-6α-((2-pyridyl)-oxy)-morphinan-7-ene (0.54 g, 1.33 mmol) is mixed with H$_2$O (20 ml) and glacial acetic acid (20 ml) and stirred for 2.5 hours at 100° C. The mixture is then concentrated by rotary evaporation in a Rotavapor at 40° C. and the residu e obtained is purified by flash chromatography (90 g silica gel; CH$_2$Cl$_2$/MeOH=9/1). The product is dissolved in H$_2$O (7 ml) and glacial acetic acid (0.7 ml) and lyophilised.
Yield: 0.436 g (1.03 mmol, 77.6%)

$^{13}$C NMR (100 MHz, CDCl$_3$) δ 176.8, 162.9, 147.2, 139.4, 139.2, 131.1, 129.8, 127.4, 123.7, 119.9, 117.7, 117.6, 111.7, 89.1, 69.2, 59.4, 46.7, 42.8, 41.7, 38.9, 33.9, 22.5, 21.7.

EXAMPLE 2

4,5α-Epoxy-6α-((5-(ethyloxycarbonyl)-2-pyridyl)-oxy)-17-methyl-morphinan-7-en-3-ol acetate 4,5α-Epoxy-6α-((5-(ethyloxycarbonyl)-2-pyridyl)-oxy)-3-methoxymethoxy-17-methyl-morphinan-7-ene NaH (0.72 g, 30 mmol) is stirred with absolute DMF (12 ml) at RT and then 4,5α-epoxy-3-methoxymethoxy-17-methyl-morphinan-7-en-6α-ol (1.9764 g, 6 mmol) in DMF (12 ml) is added. After the development of gas has ceased, a solution of ethyl 2-chloro-nicotinate (5.568 g, 30 mmol) in absolute DMF (8 ml) is added at RT. After 1 hour at RT this reaction mixture is poured onto H$_2$O (100 ml) and extracted 3 times with CH$_2$Cl$_2$ (60 ml). The combined organic phases are dried with Na$_2$SO$_4$, concentrated by rotary evaporation and the residue is purified by flash chromatography (90 g silica gel, CH$_2$Cl$_2$MeOH=9/1). Yield: 2.53 g (5.29 mmol, 88%)

$^{13}$C NMR (100 MHz, CDCl$_3$) δ 165.7, 165.6, 150.0, 148.4, 140.0, 139.1, 131.6, 129.7, 129.1, 120.6, 119.5, 118.9, 111.3, 96.3, 89 .1, 70.1, 61.2, 59.4, 46.9, 4 3.4, 43.3, 41.1, 35.8, 20.9, 14.6.

4,5α-Epoxy-17-methyl-6α-((5-(ethyloxycarbonyl)-2-pyridyl)-oxy)-17-methyl -morphinan-7-en-3-ol acetate 4,5α-Epoxy-6α-((5-(ethyloxycarbonyl)-2-pyridyl)-oxy)-3-5 methoxymethoxy-17-methyl-morphinan-7-ene (0.957 g, 2 mmol): is mixed with H$_2$O (30 ml) and glacial acetic acid (30 ml) and stirred for 6 hours at 100° C. The mixture is then concentrated at 40° C. using a Rotavapor and the residue obtained is purified by flash chromatography (90 g silica gel; CH$_2$Cl$_2$/MeOH=9/1). The product is dissolved in H$_2$O (6 ml) and glacial acetic acid (0.6 ml) and lyophilised. Yield: 0.70 g (1.42 mmol, 70.8%)

$^{13}$C NMR (100 MHz, CDCl$_3$) δ 176.4, 165.3, 149.7, 139.9, 138.8, 129.9, 129.6, 127.9, 124.1, 120.5, 119.6, 117.2, 110.9, 88.6, 69.6, 61.0, 59.0, 46.4, 42.6, 41.7, 38.9, 33.9, 22.1, 21.2, 14.3.

The following compounds were prepared analogously:

EXAMPLE 3

4,5α-Epoxy-3-methoxymethoxy-6α-[2'-pyridyl]oxy-17-methyl-morphin-7-ene $C_{27}H_{30}N_2O_6$
MW:478.55 gmol$^{-1}$ $^{13}$C NMR (100 MHz, CDCl$_3$) δ 165.4, 165.3, 149.7, 148.1, 139.6, 138.8, 131.2, 129.3, 129.2, 128.8, 120.2, 119.1, 118.6, 111.0, 96.0, 88.8, 69.8, 60.8, 59.0, 56.2, 46.3, 43.0, 42.9, 40.8, 35.4, 20.5, 14.3.

EXAMPLE 4

4,5α-Epoxy-6α-[2'-pyridyl]oxy-17-methyl-morphin-7-en-3-ol acetate $C_{25}H_{26}N_2O_5 \cdot AcOH = C_{27}H_{30}N_2O_7$
MW:494.55 gmol$^{-1}$ $^{13}$C NMR (100 MHz, CDCl$_3$) δ 176.4, 165.3, 149.7, 145.6, 139.9, 138.8, 129.9, 129.6, 127.9, 124.1, 120.5, 119.6, 117.2, 110.9, 88.6, 69.6, 61.0, 59.0, 46.4, 42.6, 41.7, 38.9, 33.9, 22.1, 21.2, 14.3.

EXAMPLE 5

4,5α-Epoxy-3-methoxymethoxy-6α-[2-pyrazinyl]oxy-17-methyl-morphin-7-ene $C_{23}H_{25}N_3O_4$
MW:407.45 gmol$^{-1}$ $^{13}$C NMR (100 MHz, CDCl$_3$) δ 159.2, 148.0, 140.3, 138.9, 136.9, 136.3, 131.1, 129.5, 129.1, 128.7, 119.3, 118.5, 95.9, 88.4, 69.6, 59.1, 56.2, 46.6, 43.1, 43.0, 40.8, 35.5, 20.6.

EXAMPLE 6

4,5α-Epoxy-6α-[2-pyrazinyl]oxy-17-methyl-morphin-7-en-3-ol acetate $C_{23}H_{25}N_3O_5$
MW:423.47 gmol$^{-1}$ $^{13}$C NMR (100 MHz, CDCl$_3$) δ 176.1, 159.3, 145.3, 140.5, 139.2, 136.3, 135.4, 129.6, 129.4, 128.1, 123.7, 119.9, 117.3, 87.7, 69.1, 59.1, 46.6, 42.2, 41.8, 39.0, 34.0, 22.1, 20.9.

EXAMPLE 7

6α-[2-Quinolinyl]oxy-4,5α-epoxy-3-methoxymethoxy-17-methyl-morphin-7-ene $C_{28}H_{28}N_2O_4$
MW:456.52 gmol$^{-1}$ $^{13}$C NMR (100 MHz, CDCl$_3$) δ 160.9, 148.4, 146.4, 138.9, 131.5, 130.1, 129.4, 128.9, 127.4, 127.3, 125.3, 124.1, 119.1, 118.7, 113.3, 96.1, 89.1, 69.1, 59.2, 56.3, 46.7, 43.1, 43.0, 40.9, 35.6, 20.7.

EXAMPLE 8

6α-[2-Quinolinyl]oxy-4,5α-epoxy-17-methyl-morphin-7-en-3-ol acetate $C_{28}H_{28}N_2O_5$
MW:472.52 gmol$^{-1}$ $^{13}$C NMR (100 MHz, CDCl$_3$) δ 176.3, 160.8, 146.3, 145.6, 139.1, 138.8, 130.7, 129.6, 129.5, 127.4, 127.3, 127.2, 125.3, 124.3, 123.8, 119.6, 117.2, 113.0, 88.7, 68.7, 59.1, 46.5, 42.4, 41.5, 38.8, 33.9, 22.0, 21.2.

EXAMPLE 9

4,5α-Epoxy-3-methoxymethoxy-17-methyl-6α-[2-pyrimidinyl]oxy-morphin-7-ene $C_{23}H_{25}N_3O_4$
MW:407.47 gmol$^{-1}$ $^{13}$C NMR (100 MHz, CDCl$_3$) δ 164.4, 159.2, 148.2, 139.1, 131.1, 129.4, 129.1, 128.6, 119.2, 118.7, 115.2, 96.2, 88.5, 71.0, 59.1, 56.3, 46.6, 43.1, 40.9, 35.6, 20.6.

EXAMPLE 10

4,5α-Epoxy-17-methyl-6α-[2-pyrimidinyl]oxy-morphin-7-en-3-ol acetate $C_{23}H_{25}N_3O_5$
MW:423.47 gmol$^{-1}$ $^{13}$C NMR (100 MHz, CDCl$_3$) δ 175.9, 164.3, 159.4, 145.9, 139.0, 129.6, 129.5, 128.1, 124.3, 119.8, 117.6, 115.5, 88.3, 70.7, 59.1, 46.5, 42.6, 41.9, 39.3, 34.1, 22.0, 21.1.

EXAMPLE 11

4,5α-Epoxy-3-methoxymethoxy-17-methyl-6α-(6'-methyl-2'-pyridyl)oxy-morphin-7-ene $C_{25}H_{28}N_2O_4$
MW:420.51 gmol$^{-1}$ $^{13}$C NMR (100 MHz, CDCl$_3$) δ 162.1, 155.9, 148.4, 138.8, 131.5, 130.4, 128.8, 128.5, 119.0, 118.7, 115.9, 107.9, 96.1, 89.3, 68.6, 59.2, 56.3, 46.7, 43.1, 43.0, 40.9, 35.6, 24.2, 20.7.

EXAMPLE 12

4,5α-Epoxy-17-methyl-6α-(6'-methyl-2'-pyridyl)oxy-morphin-7-en-3-ol acetate $C_{25}H_{28}N_2O_5$
MW:436.51 gmol$^{-1}$ $^{13}$C NMR (100 MHz, CDCl$_3$) δ 175.0, 162.0, 156.2, 145.7, 139.1, 138.7, 130.9, 129.7, 127.2, 124.2, 119.5, 117.1, 116.2, 107.7, 89.2, 68.5, 59.2, 46.6, 42.6, 41.9, 39.2, 34.1, 24.2, 22.0, 21.2.

EXAMPLE 13

4,5α-Epoxy-6α-(3'-ethoxycarbonyl-pyrid-2-yl)oxy-3-methoxymethoxy-17-methyl-morphin-7-ene $C_{27}H_{30}N_2O_6$
MW:478.55 gmol$^{-1}$ $^{13}$C NMR (100 MHz, CDCl$_3$) δ 165.3, 160.9, 150.2, 148.3, 141.2, 138.9, 131.4, 129.8, 128.8, 119.1, 119.0, 116.6, 114.9, 96.2, 88.9, 70.2, 61.0, 59.1, 56.2, 46.7, 43.1, 43.0, 40.9, 35.6, 20.6, 14.1.

EXAMPLE 14

4,5α-Epoxy-6α(3'-ethoxycarbonyl-pyrid-2-yl)oxy-17-methyl-morphin-7-en-3-ol acetate $C_{27}H_{30}N_2O_7$
MW: 494.55 gmol$^{-1}$
$^{13}$C NMR (100 MHz, CDCl$_3$) δ 176.3, 165.4, 160.5, 150.1, 146.1, 140.8, 139.3, 130.5, 129.3, 126.5, 123.1, 119.7, 118.1, 116.8, 115.0, 87.9, 68.8, 61.4, 59.2, 46.5, 41.8, 41.1, 38.0, 33.0, 22.0, 21.4, 14.1.

EXAMPLE 15

4,5α-Epoxy-3-methoxymethoxy-6α-(6'-methoxy-2'-pyridyl)oxy-17-methyl-morphin-7-ene $C_{25}H_{28}N_2O_5$
MW: 436.51 gmol$^{-1}$
$^{13}$C NMR (100 MHz, CDCl$_3$) δ 162.9, 161.6, 148.5, 141.1, 138.8, 131.3, 130.0, 128.8, 128.7, 119.1, 118.7, 102.2, 101.2, 96.1, 89.6, 69.4, 59.1, 56.3, 53.3, 46.6, 43.2, 43.1, 41.1, 35.8, 20.6.

EXAMPLE 16

4,5α-Epoxy-6α-(6'-methoxy-2'-pyridyl)oxy-17-methyl-morphin-7-en-3-ol acetate $C_{25}H_{28}N_2O_6$
MW: 452.51 gmol$^{-1}$
$^{13}$C NMR (100 MHz, CDCl$_3$) δ 176.2, 163.0, 161.5, 145.6, 141.3, 13.8, 130.7, 129.4, 127.0, 123.8, 119.7, 117.2, 101.8, 101.6, 89.3, 68.7, 59.2, 53.5, 46.6, 42.2, 41.6, 38.8, 21.8, 21.3.

EXAMPLE 17

4,5α-Epoxy-6α-(6-ethoxycarbonyl-2-pyridyl)oxy-3-methoxymethoxy-17-methyl-morphin-7-ene $C_{27}H_{30}N_2O_6$
MW: 478.55 gmol$^{-1}$
$^{13}$C NMR (100 MHz, CDCl$_3$) δ 165.0, 162.3, 148.5, 145.5, 139.2, 138.8, 131.5, 129.7, 129.0, 128.9, 119.1, 118.7, 118.6, 115.4, 96.1, 88.8, 69.6, 61.4, 59.2, 56.3, 46.7, 43.1, 43.0, 40.8, 35.6, 20.6, 14.3.

EXAMPLE 18

4,5α-Epoxy-6α-(6-ethoxycarbonyl-2-pyridyl)oxy-17-methyl-morphin-7-en-3-ol acetate $C_{27}H_{30}N_2O_7$
MW: 494.55 gmol$^{-1}$
$^{13}$C NMR (100 MHz, CDCl$_3$) δ 176.2, 165.0, 162.3, 145.6, 145.5, 139.5, 138.8, 130.4, 129.5, 127.2, 123.7, 119.7, 118.9, 117.2, 115.2, 88.5, 61.6, 59.2, 46.5, 42.3, 41.5, 38.6, 33.6, 21.9, 21.4, 14.3.

EXAMPLE 19

5α,6α-7,8-Didehydro-4,5-epoxy-3-methoxymethoxy-17-methyl-6-[3-(trifluoromethyl)-2-pyridyl]oxy-morphinane $C_{25}H_{25}F_3N_2O_4$
MW: 474.48 gmol$^{-1}$
$^{13}$C NMR (100 MHz, CDCl$_3$) δ 159.2, 150.0, 147.8, 139.0, 136.4, 136.3, 136.2, 130.9, 129.1, 129.0, 128.3, 124.0, 121.4, 119.0, 118.2, 116.1, 113.6, 113.2, 112.9, 112.6, 95.7, 88.4, 70.1, 58.8, 55.8, 46.3, 42.9, 42.8, 40.6, 35.4, 20.3.

EXAMPLE 20

5α,6α-7,8-Didehydro-4,5-epoxy-17-methyl-6-[3-(trifluoromethyl)-2-pyridyl]oxy-morphinan-3-ol acetate $C_{25}H_{25}F_3N_2O_5$
MW: 490.48 gmol$^{-1}$
$^{13}$C NMR (100 MHz, CDCl$_3$) δ 176.6, 159.3, 150.3, 145.6, 139.3, 136.7, 136.6, 130.2, 129.3, 127.1, 124.2, 123.2, 121.5, 119.6, 117.3, 116.5, 113.4, 113.1, 87.9, 69.5, 59.2, 46.5, 42.2, 41.3, 38.4, 33.5, 22.2, 21.2.

EXAMPLE 21

(5α,6α)-7,8-Didehydro-4,5-epoxy-3-methoxymethoxy-17-methyl-6-[5-(trifluoromethyl)-2-pyridyl]oxy-morphinane $C_{25}H_{25}F_3N_2C_4$
MW: 490.48 gmol$^{-1}$
$^{13}$C NMR (100 MHz, CDCl$_3$) δ 164.6, 147.9, 144.6, 144.5, 138.7, 135.6, 131.0, 129.1, 129.0 128.6, 125.2, 122.5, 120.6, 120.2, 119.9, 119.6, 119.1, 118.4, 111.3, 95.8, 88.4, 69.7, 58.9, 56.0, 46.4, 42.8, 40.6, 35.3, 20.3.

EXAMPLE 22

(5α,6α)-7,8-Didehydro-4,5-epoxy-17-methyl-6-[5-(trifluoromethyl)-2-pyridyl]oxy-morphinan-3-ol acetate $C_{25}H_{25}F_3N_2O_5$
MW: 490.48 gmol$^{-1}$
$^{13}$C NMR (100 MHz, CDCl$_3$) δ 176.7, 164.6, 145.7, 144.7, 139.3, 136.0, 130.1, 129.2, 127.3, 125.3, 123.0, 122.6, 120.7, 120.4, 119.7, 117.6, 111.5, 881, 69.5, 59.2, 46.5, 42.2, 41.3, 38.3, 33.4, 22.1, 21.4.

EXAMPLE 23

(5α,6α)-6-(3-Cyano-2-pyridyl)oxy-7,8-didehydro-4,5-epoxy-3-methoxymethoxy-17-methyl-morphinane $C_{25}H_{25}N_3O_4$
MW: 431.50 gmol$^{-1}$
$^{13}$C NMR (100 MHz, CDCl$_3$) δ 162.8, 151.0, 147.8, 143.2, 139.3, 130.9, 129.4, 128.9, 128.4, 119.4, 118.2, 1116.8, 114.8, 97.1, 96.1, 88.1, 70.6, 59.1, 56.3, 46.6, 43.1, 42.9, 40.8, 35.5, 20.5.

EXAMPLE 24

(5α,6α)-6-(3-Cyano-2-pyridyl)oxy-7,8-didehydro-4,5-epoxy-17-methyl-morphinan-3-ol acetate $C_{25}H_{25}N_3O_5$
MW: 447.50 gmol$^{-1}$
$^{13}$C NMR (100 MHz, CDCl$_3$) δ 176.6, 162.8, 151.1, 145.7, 143.2, 139.5, 129.7, 129.1, 127.4, 122.9, 119.7, 117.7, 117.1, 115.1, 97.1, 87.6, 70.3, 59.2, 46.5, 42.0, 41.3, 38.2, 33.3, 22.1, 21.3.

EXAMPLE 25

(5α,6α)-6-(4-Cyano-2-pyridyl)oxy-7,8-didehydro-4,5-epoxy-3-methoxymethoxy-17-methyl-morphinane $C_{25}H_{25}N_3O_4$ MW: 431.50 gmol$^{-1}$ $^{13}$C NMR (100 MHz, CDCl$_3$) δ 162.8, 148.1, 147.8, 138.8, 131.0, 129.3, 128.9, 128.5, 122.5, 119.2, 118.2, 117.8, 116.2, 114.4, 95.7, 88.3, 69.8, 59.0, 56.1, 46.5, 42.9, 42.8, 10.6, 35.3, 20.4.

EXAMPLE 26

(5α,6α)-6-(4-Cyano-2-pyridyl)oxy-7,8-didehydro-4,5-epoxy-17-methyl-morphinan-3-ol acetate $C_{25}H_{25}N_3O_5$ MW: 447.50 gmol$^{-1}$ $^{13}$C NMR (100 MHz, CDCl$_3$) δ 176.5, 162.7, 148.1, 145.4, 139.1, 129.9, 129.1, 127.5, 123.0, 122.7, 119.9, 118.2, 117.6, 116.3, 114.4, 88.1, 69.4, 59.2, 46.5, 42.2, 41.2, 38.2, 33.3, 21.9, 21.4.

EXAMPLE 27

4α,5α-Epoxy-3-methoxymethoxy-17-methyl-6α-[5-pyrrolidinylcarbamoyl-)-2-pyridyl]oxy-morphin-7-ene $C_{29}H_{33}N_3O_5$ MW: 503.60 gmol$^{-1}$ $^{13}$C NMR (100 MHz, CDCl$_3$) δ 167.2, 163.4, 148.2, 146.2, 138.7, 138.4, 131.3, 129.5, 129.1, 128.8, 126.4, 119.1, 118.6, 111.0, 96.0, 88.9, 69.6, 59.0, 56.2, 49.7, 46.5, 46.4, 43.0, 40.8, 35.5, 26.5, 24.3, 20.6.

EXAMPLE 28

4α,5α-Epoxy-17-methyl-6α-[5-pyrrolidinylcarbamoyl-)-2-pyridyl]oxy-morphin-7-en-3-ol acetate $C_{29}H_{33}N_3O_6$ MW: 519.60 gmol$^{-1}$ $^{13}$C NMR (100 MHz, CDCl$_3$) δ 176.3, 167.3, 163.3, 146.1, 145.8, 139.2, 138.6, 130.2, 129.3, 127.4, 126.4, 123.2, 119.5, 117.5, 111.0, 88.3, 69.3, 59.1, 49.7, 46.5, 46.4, 42.3, 41.4, 38.5, 33.6, 26.4, 24.3, 22.1, 21.3.

EXAMPLE 29

4α,5α-Epoxy-3-methoxymethoxy-17-methyl-6α-[3-pyrrolidinylcarbamoyl)-2-pyridyl]oxy-morphin-7-ene $C_{29}H_{33}N_3O_5$ MW: 503.60 gmol$^{-1}$ $^{13}$C NMR (100 MHz, CDCl$_3$) δ 165.6, 157.9, 148.5, 147.6, 138.8, 137.9, 131.3, 129.7, 129.2, 128.9, 121.7, 118.9, 118.4, 117.2, 96.1, 89.5, 70.7, 58.8, 56.2, 47.4, 46.4, 45.7, 43.5, 43.0, 41.0, 35.8, 25.9, 24.3, 20.6.

EXAMPLE 30

4α,5α-Epoxy-17-methyl-6α-[3-pyrrolidinylcarbamoyl)-2-pyridyl]oxy-morphin-7-en-3-ol acetate $C_{29}H_{33}N_3O_6$ MW: 519.60 gmol$^{-1}$ $^{13}$C NMR (100 MHz, CDCl$_3$) δ 176.2, 166.6, 157.7, 147.8, 145.9, 139.6, 137.1, 130.4, 129.0, 126.6, 122.2, 121.7, 119.6, 118.9, 117.9, 87.0, 68.7, 59.3, 47.8, 46.5, 45.8, 41.4, 41.0, 37.8, 32.9, 25.7, 24.3, 21.8, 21.4.

EXAMPLE 31

6α-[5-(Dimethylcarbamoyl-)-2-pyridyl]oxy-4,5α-epoxy-3-methoxymethoxy-17-methyl-morphin-7-ene $C_{27}H_{31}N_3O_5$ MW: 477.57 gmol$^{-1}$ $^{13}$C NMR (100 MHz, CDCl$_3$) δ 169.2, 163.3, 148.2, 146.1, 138.7, 138.3, 131.3, 129.5, 129.1, 128.8, 125.4, 119.1, 118.6, 111.1, 96.0, 88.9, 69.6, 59.0, 56.2, 46.5, 43.0, 42.9, 40.7, 35.4, 20.6.

EXAMPLE 32

6α-[5-(Dimethylcarbamoyl-)-2-pyridyl]oxy-4,5α-epoxy-17-methyl-morphin-7-en-3-ol acetate $C_{27}H_{31}N_3O_6$ MW: 493.57 gmol$^{-1}$ $^{13}$C NMR (100 MHz, CDCl$_3$) δ 176.3, 169.4, 163.2, 145.9, 145.7, 139.3, 138.5, 130.5, 129.0, 126.8, 125.4, 122.5, 119.6, 117.6, 111.0, 88.2, 69.0, 59.3, 46.5, 42.0, 41.0, 38.0, 33.1, 21.7, 21.6.

EXAMPLE 33

4α,5α-Epoxy-3-methoxymethoxy-17-methyl-6α-[4 (pyrrolidinylcarbamoyl-)-2-pyridyl]oxy-morphin-7-ene $C_{29}H_{33}N_3O_5$ MW: 503.60 gmol$^{-1}$ $^{13}$C NMR (100 MHz, CDCl$_3$) δ 167.1, 162.9, 148.3, 147.6, 147.2, 138.8, 131.3, 129.7, 129.1, 128.8, 119.1, 118.6, 114.8, 109.2, 96.0, 89.1, 69.6, 59.0, 56.3, 49.1, 46.6, 46.0, 43.1, 40.8, 35.5, 26.2, 24.3, 20.6.

EXAMPLE 34

4α,5α-Epoxy-17-methyl-6α-[4 (pyrrolidinylcarbamoyl-)-2-pyridyl]oxy-morphin-7-en-3-ol acetate $C_{27}H_{33}N_3O_6$ MW: 519.60 gmol$^{-1}$ $^{13}$C NMR (100 MHz, CDCl$_3$) δ 176.2, 167.1, 162.7, 147.5, 147.2, 145.7, 139.1, 130.3, 129.4, 127.5, 13.4, 119.6, 117.4, 114.9, 109.2, 88.4, 69.2, 59.1, 49.1, 46.4, 46.1, 42.4, 41.5, 38.6, 33.7, 26.2, 24.3, 22.1, 21.3.

EXAMPLE 35

6α-[4-(Dimethylcarbamoyl-)-2-pyridyl]oxy-4,5α-epoxy-3-methoxymethoxy-17-methyl-morphin-7-ene $C_{27}H_{31}N_3O_5$
MW: 477.57 gmol$^{-1}$
$^{13}$C NMR (100 MHz, CDCl$_3$) δ 168.9, 162.9, 148.2, 147.3, 146.9, 138.8, 131.3, 129.7, 129.1, 128.8, 119.1, 118.6, 114.8, 109.2, 96.0, 89.1, 69.6, 59.0, 56.2, 46.6, 43.1, 43.0, 40.8, 39.0, 35.5, 35.1, 20.6.

EXAMPLE 36

6α-[4-(Dimethylcarbamoyl-)-2-pyridyl]oxy-4,5α-epoxy-17-methyl-morphin-7-en-3-ol acetate $C_{27}H_{31}N_3O_6$
MW: 493.57 gmol$^{-1}$
$^{13}$C NMR (100 MHz, CDCl$_3$) δ 176.3, 169.1, 162.7, 147.3, 146.8, 145.7, 139.3, 130.6, 129.1, 126.8, 122.6, 119.7, 117.6, 114.9, 109.2, 88.1, 69.0, 59.3, 46.5, 42.1, 41.1, 39.1, 38.1, 35.1, 33.2, 21.8, 21.5.

EXAMPLE 37

6α-[(5-Cyano-2-pyridyl)oxy-4,5α-epoxy-3-methoxymethoxy-17-methyl-morphin-7-ene $C_{25}H_{25}N_3O_4$
MW: 431.50 gmol$^{-1}$
$^{13}$C NMR (100 MHz, CDCl$_3$) δ 164.7, 151.7, 147.9, 141.1, 138.8, 131.1, 129.6, 128.7, 119.3, 118.5, 117.1, 112.1, 102.8, 95.9, 88.4, 70.2, 59.0, 56.2, 46.6, 43.0, 42.9, 40.7, 35.4, 20.5.

EXAMPLE 38

6α-[(5-Cyano-2-pyridyl)oxy-4,5α-epoxy-17-methyl-morphin-7-en-3-ol acetate $C_{25}H_{25}N_3O_5$
MW: 447.50 gmol$^{-1}$
$^{13}$C NMR (100 MHz, CDCl$_3$) δ 176.6, 164.5, 151.6, 145., 141.4, 139.2, 129.9, 129.0, 127.1, 122.6, 119.9, 117.6, 117.0, 112.1, 103.00, 87.8, 69.5, 59.3, 46.6, 41.9, 41.0, 37.9, 33.0, 21.7, 21.5.

EXAMPLE 39

6α-[3-(Dimethylcarbamoyl-)-2-pyridyl]oxy-4,5α-epoxy-3-methoxymethoxy-17-methyl-morphin-7-ene $C_{27}H_{31}N_3O_5$
MW: 477.57 gmol$^{-1}$
$^{13}$C NMR (100 MHz, CDCl$_3$) δ 167.5, 157.7, 147.7, 138.9, 138.2, 131.3, 129.7, 129.2, 128.8, 120.6, 119.0, 117.3, 96.0, 89.4, 70.4, 58.9, 56.2, 50.6, 46.4, 43.4, 43.1, 40.8, 38.4, 35.7, 34.9, 20.6.

EXAMPLE 40

6α-[3-(Dimethylcarbamoyl-)-2-pyridyl]oxy-4,5α-epoxy-17-methyl-morphin-7-en-3-ol acetate $C_{27}H_{31}N_3O_6$
MW: 493.57 gmol$^{-1}$
$^{13}$C NMR (100 MHz, CDCl$_3$) δ 176.2, 157.8, 147.8, 139.5, 137.3, 130.4, 129.2, 126.9, 122.7, 120.9, 119.7, 118.0, 87.1, 68.6, 59.3, 46.5, 41.2, 38.4, 38.0, 35.1, 33.1, 21.8, 21.4.

EXAMPLE 41

4,5α-Epoxy-6α-[4-methoxycarbonyl-2-pyridyl]oxy-3-methoxymethoxy-17-methyl-morphin-7-ene $C_{26}H_{26}N_2O_6$
MW: 464.52 gmol$^{-1}$
$^{13}$C NMR (100 MHz, CDCl$_3$) δ 165.5, 163.5, 148.3, 147.4, 140.4, 138.9, 129.7, 129.1, 128.8, 119.2, 118.5, 116.1, 111.9, 96.0, 88.9, 69.7, 59.1, 56.4, 53.4, 46.6, 43.1, 40.9, 35.5, 20.6.

EXAMPLE 42

4,5α-Epoxy-6α-(4-methoxycarbonyl-2-pyridyl)oxy-17-methyl-morphin-7-en-3-ol acetate $C_{26}H_{28}N_2O_7$
MW: 480.52 gmol$^{-1}$
$^{13}$C NMR (100 MHz, CDCl$_3$) δ 176.2, 165.4, 163.3, 147.5, 145.8, 140.5, 138.8, 130.1, 129.6, 127.8, 124.0, 119.6, 117.2, 116.3, 111.7, 88.7, 69.6, 59.0, 42.7, 46.4, 42.7, 41.7, 39.0, 34.0, 22.1, 21.2.

EXAMPLE 43

6α-[5-(Diethylcarbamoyl)-2-pyridyl]oxy-4,5α-epoxy-3-methoxymethoxy-17-methyl-morphin-7-ene $C_{29}H_{35}N_3O_5$
MW: 505.62 gmol$^{-1}$
$^{13}$C NMR (100 MHz, CDCl$_3$) δ 168.9, 163.1, 148.2, 145.0, 138.8, 137.7, 131.3, 129.2, 128.9, 126.4, 119.1, 118.6, 111.2, 96.1, 89.0, 69.6, 59.0, 56.2, 46.6, 43.1, 43.0, 40.8, 35.5, 20.6.

EXAMPLE 44

6α-[5-(Diethylcarbamoyl)-2-pyridyl]oxy-4,5α-epoxy-17-methyl-morphin-7-en-3-ol acetate $C_{29}H_{35}N_3O_6$
MW: 521.62 gmol$^{-1}$
$^{13}$C NMR (100 MHz, CDCl$_3$) δ 176.4, 169.3, 163.0, 145.6, 144.8, 139.3, 138.0, 130.7, 128.9, 130.7, 128.9, 126.5, 126.3, 122.3, 119.8, 117.6, 111.1, 88.1, 68.7, 59.4, 46.7, 41.8, 41.0, 37.8, 32.9, 21.6, 21.4.

EXAMPLE 45

6α-[6-(Diethylcarbamoyl)-2-pyridyl]oxy-4,5α-epoxy-3-methoxymethoxy-17-methyl-morphin-7-ene $C_{29}H_{35}N_3O_5$
MW: 505.62 gmol$^{-1}$
$^{13}$C NMR (100 MHz, CDCl$_3$) δ 168.1, 161.4, 152.3, 148.5, 139.5, 138.8, 131.3, 129.7, 129.1, 128.9, 119.1, 118.7, 118.7, 116.6, 112.4, 96.1, 89.3, 69.4, 59.0, 56.3, 46.5, 43.2, 43.1, 42.9, 41.1, 39.9, 35.7, 20.6, 14., 12.8.

EXAMPLE 46

6α-[6-(Diethylcarbamoyl)-2-pyridyl]oxy-4,5α-epoxy-17-methyl-morphin-7-en-3-ol acetate $C_{29}H_{35}N_3O_6$
MW: 521.62 gmol$^{-1}$
$^{13}$C NMR (100 MHz, CDCl$_3$) δ 176.2, 168.1, 161.4, 152.2, 145.8, 139.7, 138.7, 129.9, 129.9, 129.8, 128.4, 124.7, 119.5, 117.0, 116.5, 112.2, 89.0, 69.3, 58.9, 46.3, 43.0, 42.9, 42.1, 40.0, 39.8, 34.6, 22.3, 20.9, 14.4, 12.8.

Example A:

Haffner test in mice, ED$_{50}$ values in nmol/kg, i.v.

| Compound | ED$_{50}$ [nmol/kg] | | | |
|---|---|---|---|---|
| | 10 min. | 30 min. | 60 min. | 120 min. |
| 1 | 2.8 | 3.3 | 9.7 | 17 |
| 2 | 1.0 | 1.4 | 3.6 | 6 |
| Morphine.HCl | 17 | 19 | 21 | 37 |

Haffner test in mice, ED$_{50}$ values in nmol/kg p.o.

| Compound | ED$_{50}$ [nmol/kg] | | | |
|---|---|---|---|---|
| | 30 min. | 60 min. | 120 min. | 180 min. |
| 1 | 54 | 64 | 109 | 170 |
| 2 | 22 | 30 | 71 | 113 |
| Morphine.HCl | 279 | 296 | 539 | 718 |

12) Further 7,8-DIHYDROMORPHINE ETHERS CONTAINING A CYCLIC GROUP

EXAMPLE 1

4,5α-Epoxy-17-methyl-6α-((2-pyridyl)-oxy)-morphinan-7-en-3-ol acetate 4,5α-Epoxy-3-methoxymethoxy-17-methyl-6α-((2-pyridyl)-oxy)-morphinan-7-ene See Example 1 of "Further ethers" above.

4,5α-Epoxy-3-methoxymethoxy-17-methyl-6α-((2-pyridyl)-oxy)-morphinane 4,5α-Epoxy-3-methoxymethoxy-17-methyl-6α-((2-pyridyl)-oxy)-morphinan-7-ene (1.0 g. 2.46 mmol) is dissolved in MeOH (40 ml), mixed with 10% Pd unactivated charcoal 800 mg and then agitated at RT under H$_2$ (1 bar over pressure) for 2 hours. The catalyst is eliminated by filtering over a filter compound and a filtrate is concentrated by rotary evaporation.

Yield: 0.94 g (2.3 mmol, 93.5%)

$^{13}$C NMR (100 MHz, CDCl$_3$) δ 162.6, 147.5, 146.1, 138.4, 138.0, 129.7, 127.0, 118.4, 117.8, 116.1, 111.3, 95.4, 88.2, 68.6, 59.7, 55.8, 46.8, 42.3, 41.8, 39.9, 36.1, 24.6, 20.2, 18.9.

4,5α-Epoxy-17-methyl-6α-((2-pyridyl)-oxy)-morphinan-3-ol acetate 4,5α-Epoxy-methoxymethoxy-17-methyl-6α-((2-pyridyl)-oxy)-morphinane (0.940 g, 2.3 mmol) is mixed with H$_2$O (35 ml) and glacial acetic acid (35 ml) and stirred for 6 hours at 100° C. The mixture is then evaporated down at 40° C. using the Rotavapor and the residue obtained is purified by flash chromatography (90 g silica gel; CH$_2$Cl$_2$/MeOH=4/1). The product is dissolved in H$_2$O (7 ml) and glacial acetic acid (0.7 ml) and lyophilised.

Yield: 0.88 g 4,5α-Epoxy-17-methyl-6α-((2-pyridyl)-oxy)-morphinan-3-ol acetate (2.07 mnol, 90.1%).

$^{13}$C NMR (100 MHz, CDCl$_3$) δ 176.5, 162.8, 146.3, 139.1, 138.8, 128.1, 121.6, 119.2, 117.6, 116.8, 111.5, 88.0, 68.5, 60.5, 47.3, 41.1, 40.9, 38.3, 34.2, 25.3, 22.1, 21.3, 18.4.

The following were prepared analogously to Example 1

EXAMPLE 2

4,5α-Epoxy-6α-((5-ethyloxycarbonyl)-2-pyridyl)-oxy)-3-methoxymethoxy-17-methyl-morphinan-3-ol acetate $^{13}$C NMR (100 MHz, CDCl$_3$) δ 165.8, 165.5, 149.8, 147.9, 139.6, 139.6, 139.5, 129.4, 125.8, 120.1, 119.4, 118.8, 111.2, 95.9, 88.1, 69.8, 61.1, 60.9, 56.4, 47.8, 42.4, 41.7, 39.8, 35.5, 25.6, 21.2, 19.0, 14.5.

EXAMPLE 3

4,5α-Epoxy-6α-((5-ethyloxycarbonyl)-2-pyridyl)-oxy)-17-methyl-morphinan-3-ol acetate $^{13}$C NMR (100 MHz, CDCl$_3$) δ 165.3, 165.2, 149.2, 145.3, 139.5, 139.2, 127.3, 120.3, 119.7, 119.7, 119.3, 118.0, 110.8, 87.0, 69.1, 61.5, 60.8, 50.0, 47.9, 41.0, 40.5, 37.8, 33.3, 25.1, 21.3, 18.0, 14.0.

EXAMPLE 4

4,5α-Epoxy-3-methoxymethoxy-6α-[21-pyridyl]oxy-17-methyl-morphine

C$_{24}$H$_{28}$N$_2$O$_4$
MW:408.50 gmol$^{-1}$ $^{13}$C NMR (100 MHz, CDCl$_3$) δ 162.9, 147.8, 146.4, 138.8, 137.4, 130.0, 127.3, 118.7, 118.2, 116.5, 111.6, 95.7, 88.5, 68.9, 60.0, 56.1, 47.1, 42.7, 42.1, 40.3, 36.4, 24.9, 20.3, 19.2.

EXAMPLE 5

4,5α-Epoxy-6α-[2'pyridyl]oxy-17-methyl-morphin-3-ol acetate

C$_{22}$H$_{24}$N$_2$O$_3$AcOH=C$_{24}$H$_{28}$N$_2$O$_5$
MW:424.50 gmol$^{-1}$ $^{13}$C NMR (100 MHz, CDCl$_3$) δ 176.5, 162.8, 146.3, 145.7, 139.1, 138.8, 128.1, 121.6, 119.2, 117.6, 116.8, 111.5, 88.0, 68.5, 47.3, 41.1, 40.9, 38.3, 34.2, 25.3, 22.1, 21.3, 18.4.

EXAMPLE 6

4,5α-Epoxy-3-methoxymethoxy-6α-[2'pyridyl]oxy-17-methyl-morphine

C$_{27}$H$_{32}$N$_2$O$_6$
MW:480.57 gmol$^{-1}$ $^{13}$C NMR (100 MHz, CDCl$_3$) δ 165.4, 165.3, 149.5, 147.5, 139.3, 139.2, 129.1, 125.4, 119.8, 119.0, 118.5, 110.9, 95.6, 87.8, 69.4, 60.8, 60.6, 56.1, 47.5, 42.0, 41.4, 19.4, 35.1, 25.3, 20.9, 18.7, 14.2.

EXAMPLE 7

4,5α-Epoxy-6α-[2pyridyl]oxy-17-methyl-morphin-3-ol acetate

C$_{25}$H$_{28}$N$_2$O$_5$AcOH=C$_{27}$H$_{32}$N$_2$O$_7$
MW:496.57 gmol$^{-1}$ $^{13}$C NMR (100 MHz, CDCl$_3$) δ 176.2, 165.5, 165.3, 149.4, 145.4, 139.7, 139.0, 128.1, 121.2, 120.0, 119.4, 117.8, 110.9, 87.66, 69.2, 61.0, 60.9, 47.6, 41.1, 40.9, 38.3, 33.8, 25.5, 21.8, 21.3, 18.3, 14.3.

EXAMPLE 8

4,5α-Epoxy-3-methoxymethoxy-6α-[2-pyrazinyl]oxy-17-methyl-morphine $C_{23}H_{27}N_3O_4$
MW:409.48 gmol$^{-1}$
$^{13}$C NMR (100 MHz, CDCl$_3$) δ 159.5, 147.3, 140.0, 138.9, 136.3, 136.2, 130.0, 119.0, 117.6, 95.6, 88.3, 69.8, 59.8, 56.1., 47.2, 42.9, 42.3, 41.3, 36.7, 29.7, 25.6, 20.3, 19.2.

EXAMPLE 9

4,5α-Epoxy-6α-[2-pyrazinyl]oxy-17-methyl-morphin-3-ol acetate $C_{23}H_{27}N_3O_5$
MW:425.48 gmol$^{-1}$
$^{13}$C NMR (100 MHz, CDCl$_3$) δ 176.5, 159.6, 145.5, 140.4, 139.2, 135.9, 135.6, 128.3, 122.1, 119.3, 117.6, 87.7, 69.6, 60.1, 47.1, 41.3, 41.2, 38.9, 34.5, 25.6, 22.3, 21.0, 18.5.

EXAMPLE 10

6α-[2-Quinolinyl]oxy-4,5α-epoxy-3-methoxymethoxy-17-methyl-morphin $C_{28}H_{30}N_2O_4$
MW:458.54 gmol$^{-1}$
$^{13}$C NMR (100 MHz, CDCl$_3$) δ 161.2, 148.0, 146.3, 138.7, 138.4, 130.3, 129.3, 127.3, 125.1, 123.8, 118.8, 118.2, 113.6, 95.8, 88.5, 69.2, 60.0, 47.1, 42.9, 42.4, 40.4, 36.8, 24.6, 20.4, 19.5.

EXAMPLE 11

6α-[2-Quinolinyl]oxy-4,5α-epoxy-17-methyl-morphin-3-ol acetate $C_{28}H_{30}N_2O_5$
MW:474.54 gmol$^{-1}$
$^{13}$C NMR (100 MHz, CDCl$_3$) δ 176.7, 161.0, 146.1, 145.9, 139.3, 138.7, 129.4, 128.0, 127.3, 127.0, 125.1, 123.9, 121.3, 119.2, 117.7, 113.3, 87.7, 68.4, 60.3, 47.1, 40.9, 40.7, 38.2, 34.1, 25.2, 22.2, 21.2, 18.4.

EXAMPLE :12

4,5α-Epoxy-3-methoxymethoxy-17-methyl-6α-[2-pyrimidinyl]oxy-morphine $C_{23}H_{27}N_3O_4$
MW:409.48 gmol$^{-1}$
$^{13}$C NMR (100 MHz, CDCl$_3$) δ 164.7, 158.8, 147.4, 138.9, 129.9, 128.9, 128.2, 119.1, 117.9, 114.6, 95.9, 88.2, 71.0, 59.8, 56.0, 46.9, 43.0, 42.6, 37.1, 25.2, 20.3, 19.6.

EXAMPLE 13

4,5α-Epoxy-17-methyl-6α-[2-pyrimidinyl]oxy-morphin-3-ol acetate $C_{23}H_{27}N_3O_5$
MW:425.48 gmol$^{-1}$
$^{13}$C NMR (100 MHz, CDCl$_3$) δ 176.6, 164.3, 159.0, 145.4, 139.2, 128.0, 122.4, 119.4, 117.8, 114.9, 87.5, 70.9, 60.1, 46.7, 41.8, 41.2, 37.4, 34.8, 24.2, 22.4, 21.1, 19.1.

Pharmacological Examples:

| Haffner test in mice, ED$_{50}$ values in nmol/kg, i.v. | | | | |
|---|---|---|---|---|
| | ED$_{50}$ [nmol/kg] | | | |
| Compound | 10 min. | 30 min. | 60 min. | 120 min. |
| 1 | 3.5 | 3.8 | 9.6 | 19 |
| 2 | 1.2 | 1.8 | 3.8 | 8 |
| 7,8-Dihydro-morphine.AcOH | 16 | 23 | 32 | 130 |
| Morphine.HCl | 17 | 19 | 21 | 37 |

| Haffner test in mice, ED$_{50}$ values in nmol/kg, p.o. | | | | |
|---|---|---|---|---|
| | ED$_{50}$ [nmol/kg] | | | |
| Compound | 30 min. | 60 min. | 120 min. | 180 min. |
| 1 | 51 | 60 | 113 | 200 |
| 3 | 26 | 30 | 72 | 132 |
| 7,8-Dihydro-morphine.AcOH | 177 | 195 | 250 | 481 |
| Morphine.HCl | 279 | 296 | 539 | 718 |

What is claimed is:

1. A morphinan derivative of the formula

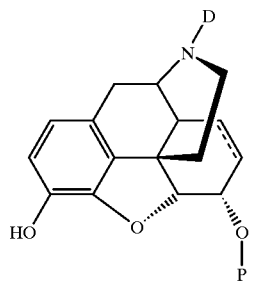

(I)

wherein

D denotes a straight-chained or branched, optionally halogenated $C_{1-4}$-alkyl group, the dotted line represent a chemical bond indicating that the compound is a morphine or 7,8-dihydromorphine derivative, P denotes a group —C(L) (R$_1$) (R$_2$), L denotes a group —A$_1$—(C(R$_3$) (R$_4$))$_k$—A$_2$—B k is an integer from 0 to 5;

R$_1$, R$_2$, R$_3$ and R$_4$ independently of one another denote hydrogen, a straight-chained or branched, $C_{1-4}$-alkyl group, a $C_{2-4}$-alkenyl group, or a group —(CH$_2$)$_x$—OR$_7$, —(CH$_2$)$_x$—OC(O)R$_7$, (CH$_2$)$_x$—F, (CH$_2$)$_x$—Cl, (CHF)$_x$—F, (CHCl)$_x$—Cl, (CF$_2$)$_x$—F, (CCl$_2$)$_x$—Cl, x is an integer from 0 to 2, A$_1$ and A$_2$ independently of each other denote a group —(CH$_2$)$_m$—, m is an integer from 0 to 4, B is a hydrogen atom or a group X, and X denotes a group —$(CH_2)_n$—OH, —$(CH_2)_n$—$CO_2R_7$, —$(CH_2)_n$—CN, —$(CH_2)_n$—$CONR_5OR_6$, —$(CH_2)_nCONR_5R_6$, —$(CH_2)_n$—$OR_5$, —$(CH_2)_n$—$COR_5$, —$(CH_2)_n$—$OC(O)R_7$, —$(CH_2)_n$—$CONR_5OR_6$, —$(CH_2O_n$—$NR_5C(O)R_6$, —$(CH_2)_n$—$SR_5$, —$(CH_2)_nS(O)R_5$, —$(CH_2)_n$—$S(O)_2NR_5R_6$, —$(CH_2)_n$—$NR_5R_6$, —$(CH_2)_n$—$NHC(O)R_5$, —$(CH_2)_n$—$NHS(O)_2R_5$, —$(CH_2)_n$—F, —$(CH_2)_n$—Cl, —$(CH_2)_n$—Br, —$(CH_2)_n$—$NO_2$ n is an integer from 0 to 4, $R_5$, $R_6$ and $R_7$ independently of one another denote hydrogen or a straight-chained or branched $C_{1-4}$-alkyl group, a $C_{2-4}$-alkenyl group or an aryl or benzyl group, or a pharmaceutically acceptable salt thereof.

2. A pharmaceutical preparation containing a compound of formula I according to claim 1 or a pharmaceutically acceptable salt thereof, in admixture with a pharmaceutically acceptable carrier, diluent or excipient.

3. A morphinan derivative according to claim 1 which is 4,5α-epoxy-6α((4-hydroxy-butyl)-oxy)-17-methyl-morphinan-7-en-3-ol acetate.

4. A pharmaceutical composition comprising a compound of formula I according to claim 1 or a pharmaceutically acceptable salt thereof, in admixture with a pharmaceutically acceptable carrier, diluent or excipient.

5. A composition of claim 4 which is an analgesic composition.

6. A method for alleviating pain which comprises administering an effective amount of the compound in claim 3 to a patient in need thereof.

7. A morphinan derivative of formula I according to claim 1, wherein D denotes a methyl group.

8. A method for alleviating pain which comprises administering an effective amount of the composition of claim 6 to a patient in need thereof.

9. A method for alleviating pain which comprises administering an effective amount of the compound in claim 1 to a patient in need thereof.

* * * * *